US011690828B2

(12) United States Patent
Jung et al.

(10) Patent No.: US 11,690,828 B2
(45) Date of Patent: Jul. 4, 2023

(54) TREATMENT OF CNS DISEASES WITH SGC STIMULATORS

(71) Applicant: Cyclerion Therapeutics, Inc., Cambridge, MA (US)

(72) Inventors: Joon Jung, Newton, MA (US); Thomas Wai-Ho Lee, Lexington, MA (US); Rajesh R. Iyengar, West Newton, MA (US); Nicholas Robert Perl, Somerville, MA (US); Peter Germano, Newton, MA (US); Maria D. Ribadeneira, Cambridge, MA (US); Kim Tang, Belmont, MA (US)

(73) Assignee: Cyclerion Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/348,359

(22) PCT Filed: Nov. 7, 2017

(86) PCT No.: PCT/US2017/060299
§ 371 (c)(1),
(2) Date: May 8, 2019

(87) PCT Pub. No.: WO2018/089328
PCT Pub. Date: May 17, 2018

(65) Prior Publication Data
US 2019/0343813 A1 Nov. 14, 2019

Related U.S. Application Data

(60) Provisional application No. 62/419,059, filed on Nov. 8, 2016.

(51) Int. Cl.
| | | |
|---|---|---|
| A61K 31/437 | (2006.01) | |
| A61K 31/506 | (2006.01) | |
| A61P 25/28 | (2006.01) | |
| A61K 31/5025 | (2006.01) | |
| A61K 31/519 | (2006.01) | |

(52) U.S. Cl.
CPC .......... *A61K 31/437* (2013.01); *A61K 31/506* (2013.01); *A61K 31/5025* (2013.01); *A61K 31/519* (2013.01); *A61P 25/28* (2018.01)

(58) Field of Classification Search
CPC .............. A61K 31/437; A61K 31/5025; A61K 31/506; A61K 31/519; A61P 25/28
See application file for complete search history.

(56) References Cited

U.S. PATENT DOCUMENTS

2010/0004235 A1* 1/2010 Schirok ................ C07D 471/04
514/234.2
2018/0065971 A1* 3/2018 Rennie ...................... A61P 1/00

FOREIGN PATENT DOCUMENTS

| CL | 49152 B1 | 9/2007 |
|---|---|---|
| WO | 2007/124854 A1 | 11/2007 |
| WO | 2017/106175 A2 | 6/2017 |
| WO | 2017/108441 A1 | 6/2017 |
| WO | 2017/121700 A1 | 7/2017 |

OTHER PUBLICATIONS

Hollas et al. Nitric Oxide 2019, 82, 59-74.*
Bhuvanendran et al. Nature Scientific Reports 2019, 9, 14507, p. 1-11.*
Sabbatini et al. Mechanisms of Aging and Development 2002, 123, 547-559.*
Correira et al., J. Neuroinflammation 2021, 18, 213, p. 1-13.*
Kurauchi et al. Neuroscience 2009, 158, 856-866.*
Purohit et al., YC-1 binding to the beta subunit of soluble guanylyl cyclase overcomes allosteric inhibition by the α subunit. Biochemistry. Jan. 14, 2014;53(1):101-14.
Roberts et al., Acidic triazoles as soluble guanylate cyclase stimulators. Bioorg Med Chem Lett. Nov. 1, 2011;21(21):6515-8.
International Search Report and Written Opinion for Application No. PCT/US2017/060299, dated Jan. 23, 2018, 10 pages.
Chien et al., Enhancement of active shuttle avoidance response by the NO-cGMP-PKG activator YC-1. Eur J Pharmacol. Aug. 20, 2008;590(1-3):233-40.
Chien et al., Enhancement of learning behaviour by a potent nitric oxide-guanylate cyclase activator YC-1. Eur J Neurosci. Mar. 2005;21(6):1679-88.
Chien et al., Enhancement of long-term potentiation by a potent nitric oxide-guanylyl cyclase activator, 3-(5-hydroxymethyl-2-furyl)-1-benzyl-indazole. Mol Pharmacol. Jun. 2003;63(6):1322-8.
He et al., NO-independent soluble guanylate cyclase agonist in pharmacological therapeutics research advances. Journal of International Pharmacy Research. Aug. 31, 2013;40(4):422-426.
Qin et al., Modulating nitric oxide signaling in the CNS for Alzheimer's disease therapy. Future Med Chem. Aug. 2013;5(12):1451-68.

* cited by examiner

*Primary Examiner* — Irina Neagu
(74) *Attorney, Agent, or Firm* — McCarter & English, LLP; Xin Zhang; James M. Alburger

(57) ABSTRACT

The present disclosure relates to the use of stimulators of soluble guanylate cyclase (sGC), pharmaceutically acceptable salts thereof and pharmaceutical formulations or dosage forms comprising them, alone or in combination with one or more additional agents, for the treatment of various CNS diseases, wherein an increase in sGC stimulation, or an increase in the concentration of nitric oxide (NO), or cyclic guanosine 3',5'-monophosphate (cGMP) or both, or an upregulation of the NO pathway is desirable.

2 Claims, 1 Drawing Sheet

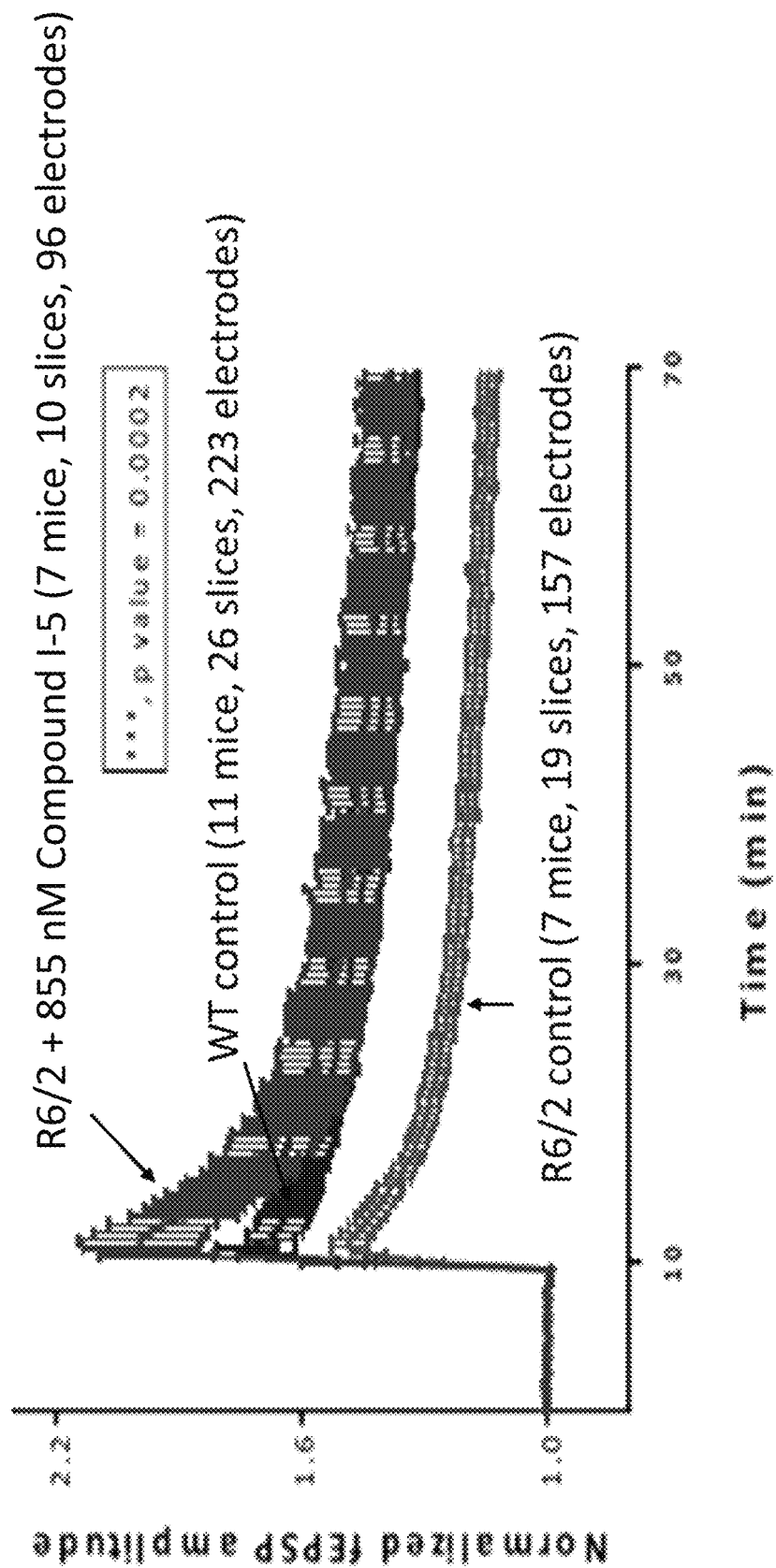

TREATMENT OF CNS DISEASES WITH SGC STIMULATORS

RELATED APPLICATIONS

This application is a 35 U.S.C. § 371 national stage filing of International Application No. PCT/US2017/060299, filed Nov. 7, 2017, which claims the benefit of the filing date under 35 U.S.C. § 119(e) of U.S. Provisional Application No. 62/419,059, filed Nov. 8, 2016. The entire contents of each of the foregoing applications are incorporated herein by reference.

FIELD OF THE INVENTION

The present disclosure relates to the use of stimulators of soluble guanylate cyclase (sGC), pharmaceutically acceptable salts thereof and pharmaceutical formulations or dosage forms comprising them, alone or in combination with one or more additional agents, for the treatment of various CNS diseases, wherein an increase in sGC stimulation, or an increase in the concentration of nitric oxide (NO) or cyclic guanosine 3',5'-monophosphate (cGMP) or both, or an upregulation of the NO pathway is desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts guanosine 5'-triphosphate (GTP) into the secondary messenger cyclic guanosine 3',5'-monophosphate (cGMP). The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III), which regulates smooth muscle relaxation and blood pressure. Experimental and clinical evidence indicates that reduced concentrations, bioavailability and/or responsiveness to endogenously-produced NO contributes to the development of a number diseases.

NO-independent, heme-dependent sGC stimulators have several important differentiating characteristics when compared to other types of sGC modulators, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed.

Compounds that stimulate sGC in an NO-independent manner offer considerable advantages over other current alternative therapies that either target the aberrant NO pathway or that target diseases that may benefit from the upregulation of the NO pathway. There is a need to develop novel stimulators of sGC. These compounds are useful for treating various diseases, wherein the diseases or disorders are ones that would benefit from sGC stimulation, or from an increase in the concentration of NO or cGMP or both, or wherein an upregulation of the NO pathway is desirable.

sGC stimulators that can cross the blood-brain barrier and penetrate the brain provide additional benefits for the treatment of diseases of the central nervous system (CNS). sGC stimulators herein described are useful for the treatment of diseases of the CNS due to their ability to cross the blood-brain barrier.

SUMMARY OF THE INVENTION

The present invention is directed to a method of treating or preventing a CNS disease, health condition or disorder in a subject in need thereof, comprising administering, alone or in combination therapy, a therapeutically effective amount of a compound or a pharmaceutically acceptable salt thereof to the subject, wherein the compound is selected from those depicted in Table I.

The invention is also directed to a pharmaceutical composition comprising a compound of Table I, or a pharmaceutically acceptable salt thereof, and at least one pharmaceutically acceptable excipient or carrier. The invention is also directed to a dosage form comprising said pharmaceutical composition.

The invention is also directed to a method of treating or preventing a CNS disease, health condition or disorder in a subject in need thereof, comprising administering, alone or in combination therapy, a pharmaceutical composition or dosage form comprising a compound depicted in Table I, or a pharmaceutically acceptable salt thereof.

The invention is further directed to the use of an sGC stimulator depicted in Table I or a pharmaceutically acceptable salt thereof, or a pharmaceutical composition or a dosage form comprising it, for the treatment of a CNS disease.

The invention is further directed to an sGC stimulator, or a pharmaceutical composition or dosage form comprising it, for use in treating a CNS disease, wherein the sGC stimulator is one depicted in Table I or a pharmaceutically acceptable salt thereof.

TABLE I

| Structure | Compound Number |
|---|---|
| [chemical structure] | I-8 |

TABLE I-continued

| Structure | Compound Number |
|---|---|
| (structure) | I-9 |
| (structure) | I-3 |
| (structure) | I-11 |
| (structure) | I-12 |
| (structure) | I-13 |
| (structure) | I-14 |
| (structure) | I-15 |
| (structure) | I-7 |

TABLE I-continued

| Structure | Compound Number |
|---|---|
| (structure) | I-6 |
| (structure) | I-10 |
| (structure) | I-5 |
| (structure) | I-4 |

TABLE I-continued

| Structure | Compound Number |
|---|---|
| (structure) | I-16 |
| (structure) | I-2 |
| (structure) | I-1 |

In some embodiments, the CNS disease, health condition or disorder is selected from Alzheimer's disease (AD), amyotrophic lateral sclerosis (ALS or Lou Gehrig's disease), Down's syndrome, dementia, vascular dementia (VD), vascular cognitive impairment, mixed dementia, Binswanger's dementia (subcortical arteriosclerotic encephalopathy), cerebral autosomal-dominant, arteriopathy with subcortical infarcts and leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment or MCI), glaucoma, Huntington's disease (or Huntington's chorea, HD), multiple sclerosis (MS), multiple system atrophy (MSA), Parkinson's disease (PD), Parkinsonism Plus, spinocerebellar ataxias, Steel-Richardson-Olszewski disease (progressive supranuclear palsy), attention deficit disorder (ADD) and attention deficit hyperactivity disorder (ADHD).

In other embodiments, the disease, health condition or disorder is a CNS disorder or condition selected from Alzheimer's disease or pre-Alzheimer's disease, mild to moderate Alzheimer's disease or moderate to severe Alzheimer's disease.

In other embodiments, the CNS disorder is selected from either traumatic (closed or open) penetrating head injuries, traumatic brain injury (TBI), non-traumatic injury to the brain (e.g., stroke (in particular, ischemic stroke), aneurism, hypoxia) or cognitive impairment or dysfunction resulting from brain injuries or neurodegenerative disorders.

In other embodiments, the CNS disease or disorder is selected from a dystonia, including for example, generalized, focal, segmental, sexual, intermediate, genetic/primary dystonia or acute dystonic reaction; or a dyskinesia, including for example, acute, chronic/tardive, and non-motor and levo-dopa induced dyskinesia (LID).

In other embodiments, the CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders (ASD), autism, Asperger's syndrome, pervasive development disorder or childhood disintegrative disorder.

In other embodiments, the CNS disorder is neuropathic pain.

In other embodiments, the CNS disorder is a psychiatric, mental, mood or affective disorder selected from a bipolar disorder, schizophrenia, general psychosis, drug-induced psychosis, a delusional disorder, a schizoaffective disorder, obsessive compulsive disorder (OCD), a depressive disorder, an anxiety disorder, a panic disorder, or post-traumatic stress disorder (PTSD).

In other embodiments, the CNS disorder is selected from chemo brain, levo-dopa induced addictive behavior, alcoholism, narcotic dependence (including but not limited to amphetamine, opiates or other substances) and substance abuse.

BRIEF DESCRIPTION OF THE DRAWINGS

FIG. 1 is a plot of the long-term potentiation of wild type (WT) mice hippocampal slices (middle curve), R6/2 mice hippocampal slices (bottom curve), and R6/2 mice hippocampal slices treated with 855 nM Compound I-5 (top curve).

DETAILED DESCRIPTION OF THE INVENTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

A compound, such as the compounds of Table I or other compounds herein described, may be present in its free form (e.g., an amorphous form, or a crystalline form or a polymorph). Under certain conditions, compounds may also form co-forms. As used herein, the term co-form is synonymous with the term multi-component crystalline form. The formation of a salt is determined by how large the difference is in the pKas between the partners that form the mixture. For purposes of this disclosure, compounds include pharmaceutically acceptable salts, even if the term "pharmaceutically acceptable salts" is not explicitly noted.

Unless only one of the isomers is drawn or named specifically, structures depicted herein are also meant to include all stereo isomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^{2}$H, $^{3}$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^{3}$H and $^{14}$C) are useful in compound and/or substrate tissue distribution assays. Tritiated (i.e., $^{3}$H) and carbon-14 (i.e., $^{14}$C) isotopes are useful for their ease of preparation and detectability. Further, substitution with heavier isotopes such as deuterium (i.e., $^{2}$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those described in the Schemes and/or in the Examples herein below, by substituting an isotopically labeled reagent for a non-isotopically labeled reagent.

Compounds

The present invention is directed to medical uses of compounds of Table I, their pharmaceutically acceptable salts thereof, pharmaceutical compositions and dosage forms.

TABLE I

| Structure | Compound Number |
|---|---|
| 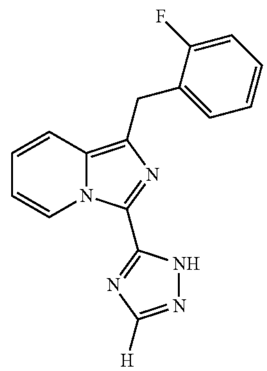 [SMILES: Fc1ccccc1Cc1nc(-c2ncn[nH]2)n2ccccc12] | I-8 |
| 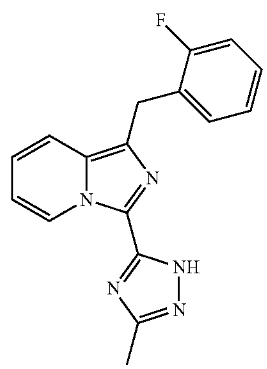 [SMILES: Cc1n[nH]c(-c2nc(Cc3ccccc3F)c3ccccn23)n1] | I-9 |
| 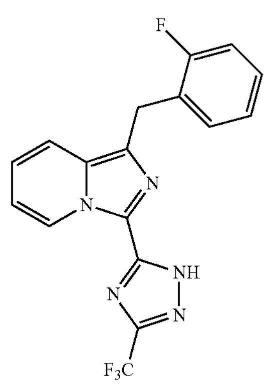 [SMILES: Fc1ccccc1Cc1nc(-c2nc(C(F)(F)F)n[nH]2)n2ccccc12] | I-3 |

TABLE I-continued

| Structure | Compound Number |
|---|---|
| 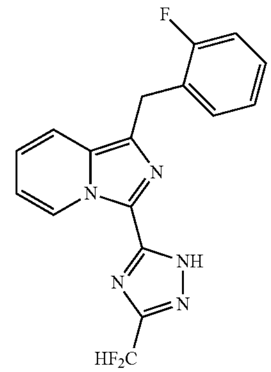 | I-11 |
| 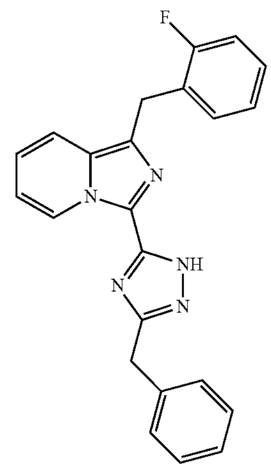 [SMILES: Fc1ccccc1Cc1nc(-c2nc(Cc3ccccc3)n[nH]2)n2ccccc12] | I-12 |
| 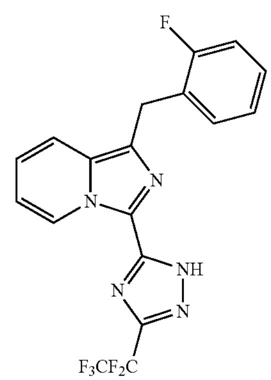 | I-13 |
| 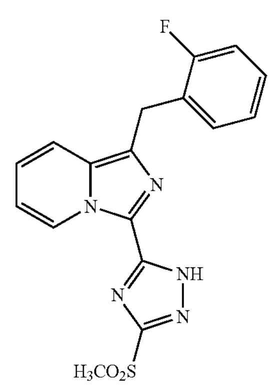 | I-14 |

TABLE I-continued
| Structure | Compound Number |
|---|---|
| 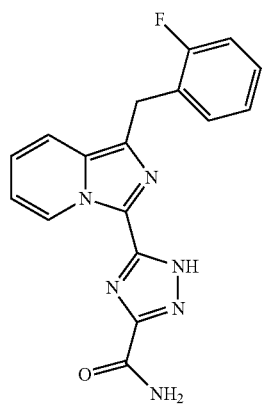 [SMILES: NC(=O)c1n[nH]c(-c2nc(Cc3ccccc3F)c3ccccn23)n1] | I-15 |
| 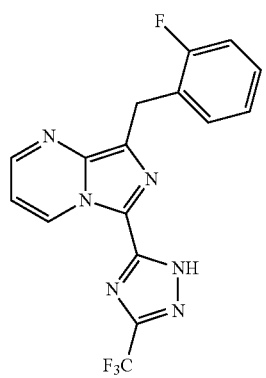 | I-7 |
| 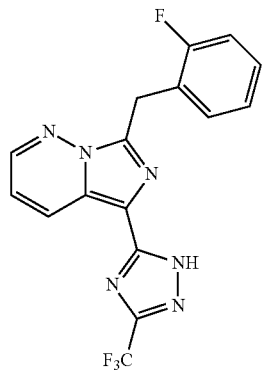 [SMILES: Fc1ccccc1Cc1nc(-c2nc(C(F)(F)F)n[nH]2)c2cccnn12] | I-6 |
| 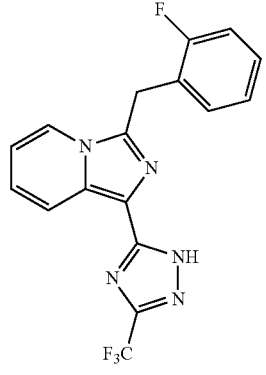 [SMILES: Fc1ccccc1Cc1nc(-c2nc(C(F)(F)F)n[nH]2)c2ccccn12] | I-10 |
TABLE I-continued
| Structure | Compound Number |
|---|---|
| 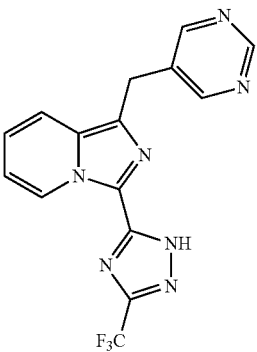 [SMILES: FC(F)(F)c1n[nH]c(-c2nc(Cc3cncnc3)c3ccccn23)n1] | I-5 |
| 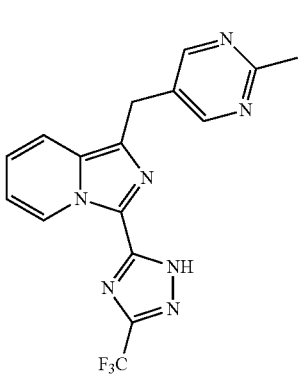 [SMILES: Cc1ncc(Cc2nc(-c3nc(C(F)(F)F)n[nH]3)n3ccccc23)cn1] | I-4 |
| 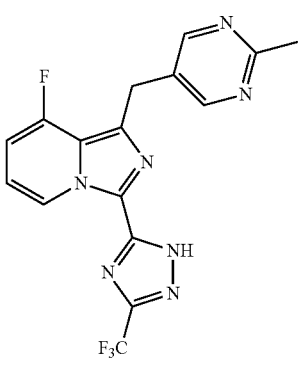 [SMILES: Cc1ncc(Cc2nc(-c3nc(C(F)(F)F)n[nH]3)n3cccc(F)c23)cn1] | I-16 |
| 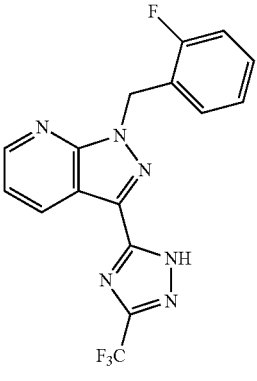 [SMILES: Fc1ccccc1Cn1nc(-c2nc(C(F)(F)F)n[nH]2)c2cccnc21] | I-2 |

TABLE I-continued

| Structure | Compound Number |
|---|---|
| (structure: pyrazolo[3,4-b]pyridine with N-methylene linked to 2-methylpyrimidine, and 3-position linked to 1H-1,2,4-triazole bearing CF₃) | I-1 |

Pharmaceutically Acceptable Salts

The phrase "pharmaceutically acceptable salt," as used herein, refers to pharmaceutically acceptable organic or inorganic salts of a compound described herein (e.g., a compound of Table I). The pharmaceutically acceptable salts of a compound described herein are used in medicine. Salts that are not pharmaceutically acceptable may, however, be useful in the preparation of a compound described herein or of a pharmaceutically acceptable salt thereof. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds described herein include those derived from the compounds with inorganic acids, organic acids, inorganic bases or organic bases. In some embodiments, the salts can be prepared in situ during the final isolation and purification of the compounds. In other embodiments the salts can be prepared from the free form of the compound in a separate synthetic step.

When a compound described herein is acidic or contains a sufficiently acidic bioisostere, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N₁-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound described herein is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

Pharmaceutical Compositions, Dosage Forms and Methods of Administration.

The compounds herein described, and their pharmaceutically acceptable salts, may be formulated as pharmaceutical compositions or "formulations".

A typical formulation is prepared by mixing a compound described herein, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound described herein is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g., enteric or slow release) preservatives, antioxidants, opaquing agents, glidants, processing aids, colorants, sweeteners, perfuming agents, flavoring agents and other known additives to provide an elegant presentation of the drug (i.e., a compound described herein or pharmaceutical composition thereof) or aid in the manufacturing of the pharmaceutical product (i.e., medicament).

The formulations may be prepared using conventional dissolution and mixing procedures. For example, the bulk drug substance (i.e., a compound described herein, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

A compound described herein, or a pharmaceutically acceptable salt thereof, is typically formulated into a pharmaceutical dosage form to provide an easily controllable dosage of the drug and to enable patient compliance with the prescribed regimen. Pharmaceutical formulations of a compound described herein, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of the compounds in Table I will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nanoparticles and nanocapsules) or in macroemulsions. Such techniques are described in Remington's: The Science and Practice of Pharmacy, $21^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g., films, or microcapsules. Examples of sustained-release matrices include polyesters, hydrogels (for example, poly (2-hydroxyethyl-methacrylate) or poly(vinylalcohol)), polylactides (such as those described in U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(–)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g., chitin, chitosan, dextran and pullulan; gum agar, gum arabic, gum karaya, locust bean gum, gum tragacanth, carrageenans, gum ghatti, guar gum, xanthan gum and scleroglucan), starches (e.g., dextrin and maltodextrin), hydrophilic colloids (e.g., pectin), phosphatides (e.g., lecithin), alginates (e.g., ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent.

For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LY) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g., methyl acrylate-methyl methacrylate copolymers, polyvinyl chloride, polyethylene), hydrophilic polymers (e.g., ethyl cellulose, cellulose acetate, cross linked polyvinylpyrrolidone (also known as crospovidone)), and fatty compounds (e.g., carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semipermeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non-limiting examples of osmotic control devices are described in U.S. patent application Ser. No. 09/495,061.

The amount of water-swellable hydrophilic polymers present in the core may range from about 5 to about 80 wt % (including for example, 10 to 50 wt %). Non-limiting examples of core materials include hydrophilic vinyl and acrylic polymers, polysaccharides such as calcium alginate, polyethylene oxide (PEO), polyethylene glycol (PEG), polypropylene glycol (PPG), poly (2-hydroxyethyl methacrylate), poly (acrylic) acid, poly (methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolate. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non-limiting examples of standard disintegrants include materials such as sodium starch glycolate (e.g., Explotab™ CLV), microcrystalline cellulose (e.g., Avicel™), microcrystalline silicified cellulose (e.g., ProSolv™) and croscarmellose sodium (e.g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. Nos. 6,419,952, 6,342,249, 5,324,280, 4,672,850, 4,627,850, 4,203,440, and 3,995,631.

As further noted above, the agents described herein may be provided in the form of microparticulates, generally ranging in size from about 10 μm to about 2 mm (including, for example, from about 100 μm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary.

Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally, although not necessarily, selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols (preferably lower molecular weight polyethylene glycols, e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 μm) can be designed using polymers able to be degraded in vivo (e.g., biodegradable polyalkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g., orally (e.g., using capsules, powders, solutions, suspensions, tablets, sublingual tablets and the like), by inhalation (e.g., with an aerosol, gas, inhaler, nebulizer or the like), to the ear (e.g., using ear drops), topically (e.g., using creams, gels, liniments, lotions, ointments, pastes, transdermal patches, etc.), ophthalmically (e.g., with eye drops, ophthalmic gels, ophthalmic ointments), rectally (e.g., using enemas or suppositories), nasally, buccally, vaginally (e.g., using douches, intrauterine devices, vaginal suppositories, vaginal rings or tablets, etc.), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound described herein that are suitable for oral administration may be prepared as discrete units such as tablets, pills, troches, lozenges, aqueous or oil suspensions, dispersible powders or granules, emulsions, hard or soft capsules, e.g., gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g., for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of an injectable, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound described herein in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a compound described herein contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound described herein may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound described herein include Tween™-60, Span™-80, cetostearyl alcohol, benzyl alcohol, myristyl alcohol, glyceryl mono-stearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound described herein or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

The present invention is directed to a method of treating or preventing a CNS disease, health condition or disorder in a subject in need thereof, comprising administering, alone or in combination therapy, a therapeutically effective amount of a compound or a pharmaceutically acceptable salt thereof to the subject, wherein the compound is selected from those depicted in Table I.

The invention is also directed to a pharmaceutical composition comprising a compound of Table I, or a pharmaceutically acceptable salt thereof, and at least one pharmaceutically acceptable excipient or carrier. The invention is also directed to a dosage form comprising said pharmaceutical composition.

The invention is also directed to a method of treating or preventing a CNS disease, health condition or disorder in a subject in need thereof, comprising administering, alone or in combination therapy, a pharmaceutical composition or dosage form comprising a compound depicted in Table I, or a pharmaceutically acceptable salt thereof.

The invention is further directed to the use of an sGC stimulator depicted in Table I or a pharmaceutically acceptable salt thereof, or a pharmaceutical composition or a dosage form comprising it, for the treatment of a CNS disease.

The invention is further directed to an sGC stimulator or a pharmaceutical composition or dosage form comprising it, for use in treating a CNS disease, wherein the sGC stimulator is one depicted in Table I or a pharmaceutically acceptable salt thereof.

In other embodiments, the compounds here disclosed are sGC stimulators that may be useful in the prevention and/or treatment of diseases and disorders characterized by increased neuroinflammation. One embodiment of the invention is a method of decreasing neuroinflammation in a subject in need thereof by administering to the subject any one of the compounds depicted in Table I or a pharmaceutically acceptable salt thereof, or a pharmaceutical composition or a dosage form comprising it.

In other embodiments, the compounds here disclosed are sGC stimulators that may be useful in the prevention and/or treatment of diseases and disorders characterized by increased neurotoxicity. One embodiment of the invention is a method of reducing neurotoxicity in a subject in need thereof by administering to the subject any one of the compounds depicted in Table I or a pharmaceutically acceptable salt thereof, or a pharmaceutical composition or a dosage form comprising it.

In other embodiments, the compounds here disclosed are sGC stimulators that may be useful in the prevention and/or treatment of diseases and disorders characterized by impaired neurorengeneration. One embodiment of the invention is a method of restoring neuroregeneration in a subject in need thereof by administering to the subject any one of the compounds depicted in Table I or a pharmaceutically acceptable salt thereof, or a pharmaceutical composition or a dosage form comprising it.

In other embodiments, the compounds here disclosed are sGC stimulators that may be useful in the prevention and/or treatment of diseases and disorders characterized by impaired synaptic function. One embodiment of the invention is a method of restoring synaptic function in a subject in need thereof by administering to the subject any one of the compounds depicted in Table I or a pharmaceutically acceptable salt thereof, or a pharmaceutical composition or a dosage form comprising it.

In other embodiments, the compounds here disclosed are sGC stimulators that may be useful in the prevention and/or treatment of diseases and disorders characterized by down-regulated neurotransmitters. One embodiment of the invention is a method of normalizing neurotransmitter in a subject in need thereof by administering to the subject any one of the compounds depicted in Table I or a pharmaceutically acceptable salt thereof, or a pharmaceutical composition or a dosage form comprising it. Specifically, the disease is Alzheimer's Disease. Specifically, the disease is Mixed Dementia.

In other embodiments, the compounds here disclosed are sGC stimulators that may be useful in the prevention and/or treatment of diseases and disorders characterized by impaired cerebral blood flow. One embodiment of the invention is a method of restoring cerebral blood flow in a subject in need thereof by administering to the subject any one of the compounds depicted in Table I or a pharmaceutically acceptable salt thereof, or a pharmaceutical composition or a dosage form comprising it. Specifically, the disease is Vascular Dementia or Alzheimer's Disease. Specifically, the disease is Mixed Dementia. In other embodiments CNS disorder is selected from either traumatic (closed or open, penetrating head injuries), traumatic brain injury (TBI), or nontraumatic (stroke (in particular, ischemic stroke), aneurism, hypoxia) injury to the brain or cognitive impairment or dysfunction resulting from brain injuries or neurodegenerative disorders.

In other embodiments, the compounds here disclosed are sGC stimulators that may be useful in the prevention and/or treatment of diseases and disorders characterized by increased neurodegeneration. One embodiment of the invention is a method of decreasing neurodegeneration in a subject in need thereof by administering to the subject any one of the compounds depicted in Table I or a pharmaceutically acceptable salt thereof, or a pharmaceutical composition or a dosage form comprising it.

In other embodiments, the compounds here disclosed are sGC stimulators are neuroprotective. In particular, the compounds depicted in Table I or a pharmaceutically acceptable salt thereof, or a pharmaceutical composition or a dosage form comprising it may be useful protect the neurons in a subject in need thereof.

In other embodiments, the compounds here disclosed are sGC stimulators that may be useful in the prevention and/or treatment of orphan pain indications. One embodiment of the invention is a method of treating an orphan pain indication in a subject in need thereof by administering to the subject any one of the compounds depicted in Table I or a pharmaceutically acceptable salt thereof, or a pharmaceutical composition or a dosage form comprising it. In particular, the orphan pain indication is selected from Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, and Tolosa-Hunt syndrome.

In other embodiments, the compounds here disclosed are sGC stimulators that may be useful in the prevention and/or treatment of altitude (mountain) sickness, cerebral small vessel disease, cerebral vasculitis, cerebral vasospasm, hepatic encephalopathy, moyamoya, Parkinson's Dysphagia, ataxia telangliectasia, autism spectrum disorder, chronic fatigue, chronic traumatic encephalopathy (CTE), cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell, concussion, retinopathy, diabetic retinopathy (including proliferative and non-proliferative), dysphagia, eye fibrosis, Fabry Disease, Gaucher Disease, glioblastoma, brain inflammation caused by cerebral malaria (SoC), brain inflammation caused by infectious disease, intellectual disability, myopic choroidal neovascularization, neuromyelitis optica, neuropathic pain with Multiple Sclerosis, neuropathic pain with shingles (herpes zoster), neuropathic pain with spine surgery, Parkinson's Dementia, peripheral and autonomic neuropathies, peripheral retinal degeneration, post-traumatic stress syndrome, post herpetic neuralgia, post-operative dementia, proliferative vitroretinopathy, radiation induced brain fibrosis, radiculopathy, refractory epilepsy, retinal vein occlusion, spinal cord injury, spinal muscular atrophy, spinal subluxations. tauopathies, and wet age-related macular degeneration.

The CNS diseases that may benefit from treatment with an sGC stimulator of the invention are those CNS diseases wherein an increase in the concentration of NO or an increase in the concentration of cGMP or both, or an upregulation of the NO pathway might be desirable.

The compounds described herein, as well as pharmaceutically acceptable salts thereof, as stimulators of sGC that are able to cross the blood-brain barrier, are useful in the prevention and/or treatment of CNS diseases, conditions and disorders which can benefit from sGC stimulation in the brain.

In some embodiments, the CNS disease, health condition or disorder is selected from Alzheimer's disease (AD), amyotrophic lateral sclerosis (ALS or Lou Gehrig's disease), Down's syndrome, dementia, vascular dementia (VD), vascular cognitive impairment, Mixed Dementia, Binswanger's dementia (subcortical arteriosclerotic encephalopathy), cerebral autosomal-dominant arteriopathy with subcortical infarcts and leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment or MCI), glaucoma, Huntington's diseases (or Huntington's chorea, HD), multiple sclerosis (MS) (including Clinically isolated syndrome (CIS), Relapsing-remitting MS (RRMS), Primary progressive MS (PPMS), and Secondary progressive MS (SPMS)), multiple system atrophy (MSA), Parkinson's disease (PD), Parkinsonism Plus, spinocerebellar ataxias, Steel-Richardson-Olszewski disease (progressive supranuclear palsy), attention deficit disorder (ADD) and attention deficit hyperactivity disorder (ADHD).

In other embodiments, the disease, health condition or disorder is a CNS disorder or condition selected from Alzheimer's disease or pre-Alzheimer's disease, mild to moderate Alzheimer's disease or moderate to severe Alzheimer's disease.

In other embodiments, the CNS disorder is selected from either traumatic (closed or open) penetrating head injuries, traumatic brain injury (TBI), including, for example, concussions and Chronic traumatic encephalopathy (CTE)), non-traumatic injury to the brain (e.g., stroke (including ischemic stroke), aneurism, hypoxia) or cognitive impairment or dysfunction resulting from brain injuries or neurodegenerative disorders.

In other embodiments, the CNS disease or disorder is selected from a dystonia, including for example, generalized, focal, segmental, sexual, intermediate, genetic/primary dystonia or acute dystonic reaction; or a dyskinesia, including for example, acute, chronic/tardive, and non-motor and levo-dopa induced dyskinesia (LID).

In other embodiments, the CNS disease or disorder is selected from disorders characterized by a relative reduction in synaptic plasticity and synaptic processes including, for example, Fragile X, Rhett's disorder, Williams syndrome, Renpenning's syndrome, autism spectrum disorders (ASD), autism, Asperger's syndrome, pervasive development disorder or childhood disintegrative disorder.

In other embodiments, the CNS disorder is neuropathic pain.

In other embodiments, the CNS disorder is a psychiatric, mental, mood or affective disorder selected from a bipolar disorder, schizophrenia, general psychosis, drug-induced psychosis, a delusional disorder, a schizoaffective disorder, obsessive compulsive disorder (OCD), a depressive disorder, an anxiety disorder, a panic disorder, post-traumatic stress disorder (PTSD).

In further embodiments, the CNS disorder is selected from age-associated memory impairment, mixed dementia, sleep wake disorders, and Sneddon's syndrome.

In further embodiments, the disease or condition is selected from acute pain, central pain syndrome, chemotherapy induced neuropathy and neuropathic pain, diabetic neuropathy, fibromyalgia, Inflammatory pain, neuropathic pain, neuropathic pain associated with a CNS disease, painful diabetic peripheral neuropathy, post-operative pain, tonic pain, and visceral pain.

In other embodiments, the CNS disorder is selected from chemo brain, levo-dopa induced addictive behavior, alcoholism, narcotic dependence (including but not limited to amphetamine, opiates or other substances) and substance abuse.

The terms "disease", "disorder", "health condition" and "condition" may be used interchangeably here to refer to an sGC, cGMP and/or NO mediated, medical or pathological condition of the CNS or to a disease of the CNS that may otherwise benefit from an upregulation of the NO pathway.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound described herein, or a pharmaceutically acceptable salt thereof, to the subject in need of the treatment. Alternatively, the invention provides the use of a compound described herein, or a pharmaceutically acceptable salt thereof, in the treatment of one of these diseases, conditions and disorders in a subject in need of the treatment.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, cerebrospinal fluid (CSF), or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or a condition that would benefit from the upregulation of the NO pathway, or the amelioration of one or more symptoms (preferably, one or more discernible symptoms) of said condition (i.e., "managing" without "curing" the condition), resulting from the administration of one or more therapies (e.g., one or more therapeutic agents such as a compound of Table I or a composition or dosage form thereof). In specific embodiments, the terms "treat", "treatment" and "treating" refer to the amelioration of at least one measurable physical parameter of an sGC, cGMP and/or NO mediated condition or a disease that would benefit from the upregulation of the NO pathway. In other embodiments the terms "treat", "treatment" and "treating" refer to the inhibition of the progression of an sGC, cGMP and/or NO mediated condition, or a disease that would benefit from the upregulation of the NO pathway, either physically by, e.g., stabilization of a discernible symptom, or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself or prior to the disorder being diagnosed.

In one embodiment, the methods of the invention are a preventative or "preemptive" measure to a patient, specifically a human, having a predisposition (e.g., a genetic predisposition) to developing an sGC, cGMP and/or NO related disease, disorder or symptom.

In other embodiments, the methods of the invention are a preventative or "preemptive" measure to a patient, specifically a human, suffering from a disease, disorder or condition that makes him at risk of developing an sGC, cGMP or NO related disease, disorder or symptom.

Compounds and compositions here described are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound of Table I or a pharmaceutically acceptable salt, composition or dosage form thereof. Use of a sGC stimulator in a biological sample is useful for a variety of purposes known to one of skill in the art. Examples of such purposes include, without limitation, biological assays and biological specimen storage.

The compounds and pharmaceutical compositions described herein can be used alone or in combination therapy for the treatment or prevention of a disease or disorder mediated, regulated or influenced by sGC, cGMP and/or NO.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When "co-administered" with other agents, e.g., when co-administered with another medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Table I or a pharmaceutically acceptable salt thereof and a second amount of an additional suitable therapeutic agent.

In one embodiment of this invention, a compound of Table I, or a pharmaceutically acceptable salt thereof, and the additional therapeutic agent are each administered in an effective amount (i.e., each in an amount which would be therapeutically effective if administered alone). In another embodiment, the compound of Table I, or pharmaceutically acceptable salt thereof, and the additional therapeutic agent are each administered in an amount which alone does not provide a therapeutic effect (a sub-therapeutic dose). In yet another embodiment, the compound of Table I can be administered in an effective amount, while the additional therapeutic agent is administered in a sub-therapeutic dose.

In still another embodiment, the compound of Table I can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Table I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Table I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of Table I, or a pharmaceutically acceptable salt thereof, either administered separately or in the same pharmaceutical composition include, but are not limited to:

(1) Endothelium-derived releasing factor (EDRF) or NO gas.

(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholino-sydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.

(3) Other substances that enhance cGMP concentrations such as protoporphyrin IX, arachidonic acid and phenyl hydrazine derivatives.

(4) Nitric Oxide Synthase substrates: for example, N-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavaline, epsilon guanidine-caproic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.

(5) Compounds which enhance eNOS transcription.

(6) NO independent heme-independent sGC activators, including, but not limited to:

BAY 58-2667 (described in patent publication DE19943635)

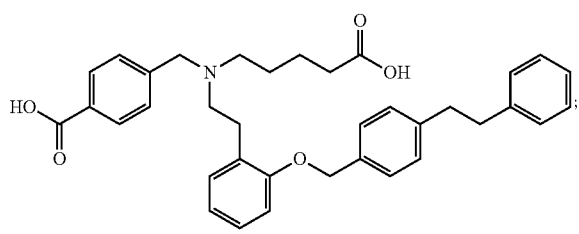 [SMILES: O=C(O)CCCCN(CCc1ccccc1OCc1ccc(CCc2ccccc2)cc1)Cc1ccc(C(=O)O)cc1]

HMR-1766 (ataciguat sodium, described in patent publication WO2000002851)

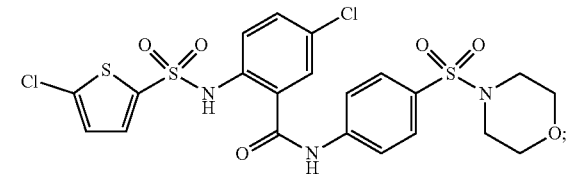 [SMILES: O=C(Nc1ccc(S(=O)(=O)N2CCOCC2)cc1)c1cc(Cl)ccc1NS(=O)(=O)c1ccc(Cl)s1]

S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851)

and

HMR-1069 (Sanofi-Aventis).

(7) Heme-dependent, NO-independent sGC stimulators including, but not limited to:

YC-1 (see patent publications EP667345 and DE19744026)

riociguat (BAY 63-2521, Adempas®, described in DE19834044)

neliciguat (BAY 60-4552, described in WO 2003095451)

vericiguat (BAY 1021189)

BAY 41-2272 (described in DE19834047 and DE19942809)

BAY 41-8543 (described in DE19834044)

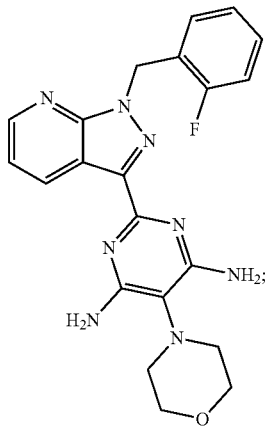 [SMILES: Nc1nc(-c2nn(Cc3ccccc3F)c3ncccc23)nc(N)c1N1CCOCC1]

etriciguat (described in WO 2003086407)

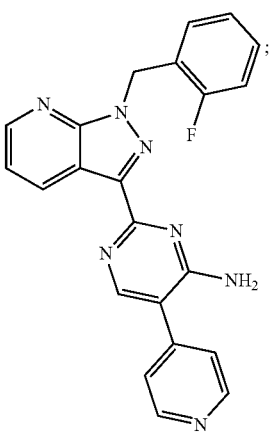 [SMILES: Nc1nc(-c2nn(Cc3ccccc3F)c3ncccc23)ncc1-c1ccncc1]

CFM-1571 (described in patent publication WO2000027394)

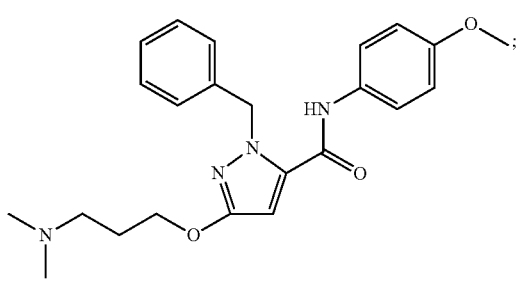

A-344905, its acrylamide analogue A-350619 and the aminopyrimidine analogue A-778935

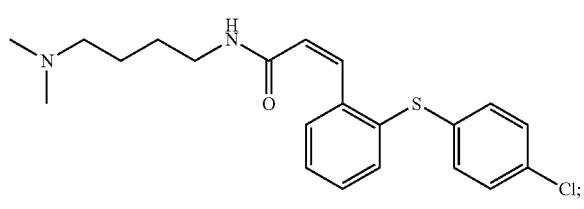

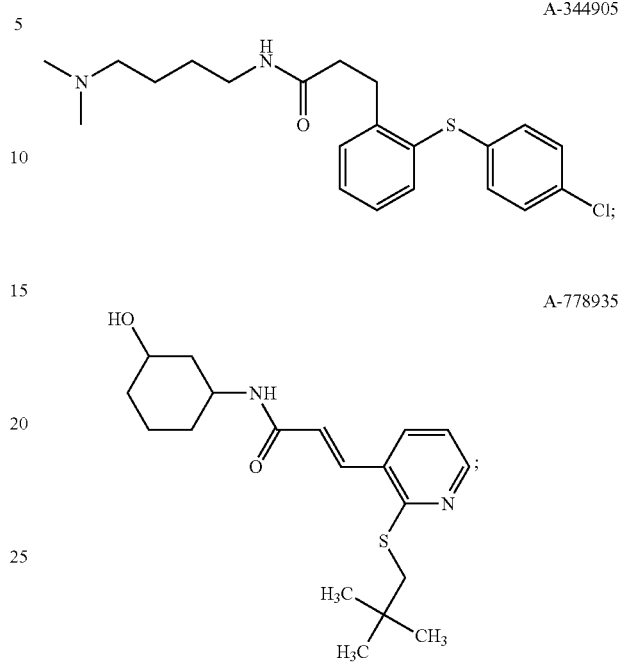

and other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and other compounds described in Tetrahedron Letters (2003), 44(48): 8661-8663.

(8) Compounds that inhibit the degradation of cGMP, such as:

PDE5 inhibitors, such as, for example, sildenafil (Viagra®) and related agents such as avanafil, lodenafil, mirodenafil, sildenafil citrate (Revatio®), tadalafil (Cialis® or Adcirca®), vardenafil (Levitra®) and udenafil; alprostadil; dipyridamole and PF-00489791;

PDE9 inhibitors, such as, for example, PF-04447943; and

PDE10 inhibitors such as, for example, PF-02545920 (PF-10).

(9) Calcium channel blockers of the following types:

dihydropyridine calcium channel blockers such asamlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), isradipine (Lomir®);

phenylalkylamine calcium channel blockers such as verapamil (Calan®, Isoptin®)

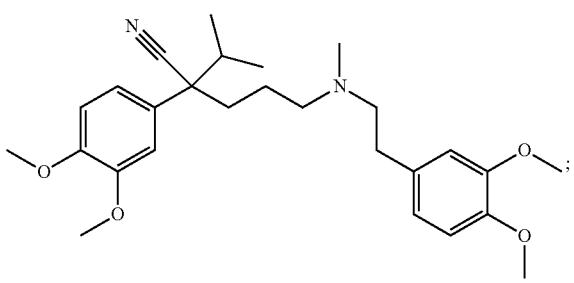

and gallopamil (Procorum®, D600);
benzothiazepines such as diltiazem (Cardizem®)

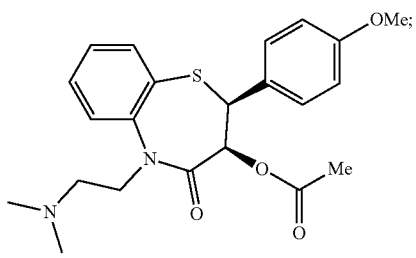 [SMILES: COc1ccc([C@@H]2Sc3ccccc3N(CCN(C)C)C(=O)[C@@H]2OC(C)=O)cc1]

and
nonselective calcium channel inhibitors such as mibefradil, bepridil, fluspirilene, and fendiline.

(10) Endothelin receptor antagonists (ERAs) such as the dual ($ET_A$ and $ET_B$) endothelin receptor antagonist bosentan (Tracleer®), sitaxentan (Thelin®) or ambrisentan (Letairis®).

(11) Prostacyclin derivatives or analogues, such as prostacyclin (prostaglandin $I_2$), epoprostenol (synthetic prostacyclin, Flolan®), treprostinil (Remodulin®), iloprost (Ilomedin®), iloprost (Ventavis®); and oral and inhaled forms of Remodulin® under development.

(12) Antihyperlipidemics such as the following types:
bile acid sequestrants like cholestyramine, colestipol, colestilan, colesevelam or sevelamer;
statins like atorvastatin, simvastatin, lovastatin, fluvastatin, pitavastatin, rosuvastatin and pravastatin;
cholesterol absorption inhibitors such as ezetimibe;
other lipid lowering agents such as icosapent ethyl ester, omega-3-acid ethyl esters, reducol;
fibric acid derivatives such as clofibrate, bezafibrate, clinofibrate, gemfibrozil, ronifibrate, binifibrate, fenofibrate, ciprofibrate, choline fenofibrate;
nicotinic acid derivatives such as acipimox and niacin;
combinations of statins, niacin and intestinal cholesterol absorption-inhibiting supplements (ezetimibe and others) and fibrates; and
antiplatelet therapies such as clopidogrel bisulfate.

(13) Anticoagulants, such as the following types:
coumarines (Vitamin K antagonists) such as warfarin (Coumadin®), cenocoumarol, phenprocoumon and phenindione;
heparin and derivatives such as low molecular weight heparin, fondaparinux and idraparinux;
direct thrombin inhibitors such as argatroban, lepirudin, bivalirudin, dabigatran and ximelagatran (Exanta®); and
tissue-plasminogen activators, used to dissolve clots and unblock arteries, such as alteplase.

(14) Antiplatelet drugs such as, for instance, topidogrel, ticlopidine, dipyridamole and aspirin.

(15) ACE inhibitors, for example the following types:
sulfhydryl-containing agents such as captopril (Capoten®) and zofenopril;
dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);
phosphonate-containing agents such as fosinopril;
naturally occurring ACE inhibitors such as casokinins and lactokinins, which are breakdown products of casein and whey that occur naturally after ingestion of milk products, especially cultured milk;
the lactotripeptides Val-Pro-Pro and Ile-Pro-Pro produced by the probiotic *Lactobacillus helveticus* or derived from casein also having ACE-inhibiting and antihypertensive functions;
other ACE inhibitors such as alacepril, delapril, cilazapril, imidapril, trandolapril, temocapril, moexipril and pirapril.

(16) Supplemental oxygen therapy.

(17) Beta blockers, such as the following types:
non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;
$β_1$-Selective agents such as cebutolol, atenolol, betaxolol, bisoprolol, celiprolol, dobutamine hydrochloride, irsogladine maleate, carvedilol, talinolol, esmolol, metoprolol and nebivolol; and
$β_2$-Selective agents such as butaxamine.

(18) Antiarrhythmic agents such as the following types:
Type I (sodium channel blockers) such as quinidine, lidocaine, phenytoin, propafenone;
Type III (potassium channel blockers) such as amiodarone, dofetilide and sotalol; and
Type V such as adenosine and digoxin.

(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.

(20) Direct-acting vasodilators such as hydralazine hydrochloride, diazoxide, sodium nitroprusside, cadralazine; other vasodilators such as isosorbide dinitrate and isosorbide 5-mononitrate.

(21) Exogenous vasodilators such as Adenocard® and alpha blockers.

(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.

(23) Bronchodilators of the following types:
short acting $β_2$ agonists, such as albutamol or albuterol (Ventolin®) and terbutaline;
long acting $β_2$ agonists (LABAs) such as salmeterol and formoterol;
anticholinergics such as pratropium and tiotropium; and
theophylline, a bronchodilator and phosphodiesterase inhibitor.

(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.

(25) Dietary supplements such as, for example omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(26) PGD2 receptor antagonists.

(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as β2-agonists like terbutaline, metaproterenol, fenoterol, isoetharine, albuterol, salmeterol, bitolterol and pirbuterol; β2-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); α-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; dipeptidyl peptidase IV inhibitors such as sitagliptin, vildagliptin, saxagliptin, alogliptin and linagliptin.

(32) HDL cholesterol-increasing agents such as anacetrapib and dalcetrapib.

(33) Antiobesity drugs such as methamphetamine hydrochloride, amfepramone hydrochloride (Tenuate®), phentermine (Ionamin®), benzfetamine hydrochloride (Didrex®), phendimetrazine tartrate (Bontril®, Prelu-2®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, metformin hydrochloride, sibutramine/metformin, bupropion SR/zonisamide SR, CORT-108297, canagliflozin, chromium picolinate, GSK-1521498, LY-377604, metreleptin, obinepitide, P-57AS3, PSN-821, salmeterol xinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and beta-lapachone.

(34) Angiotensin receptor blockers such as losartan, valsartan, candesartan, cilexetil, eprosaran, irbesartan, telmisartan, olmesartran, medoxomil, azilsartan and medoxomil.

(35) Renin inhibitors such as aliskiren hemifumarate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) PDE-3 inhibitors such as amrinone, milrinone, enoximone, vesnarinone, pimobendan, and olprinone.

(46) Adenylate cyclase activators such as colforsin dapropate hydrochloride.

(47) Positive inotropic agents such as digoxin and metildigoxin; metabolic cardiotonic agents such as ubidecarenone; brain natriuretic peptides such as nesiritide.

(48) Drugs used for the treatment of erectile dysfunction such as alprostadil, aviptadil, and phentolamine mesilate.

(49) Drugs used in the treatment of obesity, including but not limited to, methamphetamine hydrochloride (Desoxyn®), amfepramone hydrochloride (Tenuate®), phentermine (Ionamin®), benzfetamine hydrochloride (Didrex®), phendimetrazine hydrochloride (Bontril®, Prelu-2®, Plegine®), mazindol (Sanorex®) and orlistat (Xenical®).

(50) Drugs used for the treatment of Alzheimer's disease and dementias such as the following types
acetyl cholinesterase inhibitors including galantamine (Razadyne®), rivastigmine (Exelon®), donepezil (Aricept®) and tacrine (Cognex®);
NMDA receptor antagonists such as memantine (Namenda®); and
oxidoreductase inhibitors such as idebenone.

(51) Psychiatric medications such as the following types:
ziprasidone (Geodon™), risperidone (Risperdal™), olanzapine (Zyprexa™), valproate;

dopamine D4 receptor antagonists such as clozapine;
dopamine D2 receptor antagonists such as nemonapride;
mixed dopamine D1/D2 receptor antagonists such as zuclopenthixol;
GABA A receptor modulators such as carbamazepine;
sodium channel inhibitors such as lamotrigine;
monoamine oxidase inhibitors such as moclobemide and indeloxazine;
pimavanserin, perospirone; and
PDE4 inhibitors such as roflumilast.

(52) Drugs used for the treatment of movement disorders or symptoms such as the following types:
catechol-O-methyl transferase inhibitors such as entacapone;
monoamine oxidase B inhibitors such as selegiline;
dopamine receptor modulators such as levodopa;
dopamine D3 receptor agonists such as pramipexole;
decarboxylase inhibitors such as carbidopa;
other dopamine receptor agonists such as pergolide, ropinirole, cabergoline;
ritigonide, istradefylline, talipexole; zonisamide and safinamide; and
synaptic vesicular amine transporter inhibitors such as tetrabenazine.

(53) Drugs used for the treatment of mood or affective disorders or OCD such as the following types
tricyclic antidepressants such as amitriptyline (Elavil®), desipramine (Norpramin®), imipramine (Tofranil®), amoxapine (Asendin®), nortriptyline and clomipramine;
selective serotonin reuptake inhibitors (SSRIs) such as paroxetine (Paxil®), fluoxetine (Prozac®), sertraline (Zoloft®), and citralopram (Celexa®);
doxepin (Sinequan®), trazodone (Desyrel®) and agomelatine;
selective norepinephrine reuptake inhibitors (SNRIs) such as venlafaxine, reboxetine and atomoxetine; dopaminergic antidepressants such as bupropion and amineptine.

(54) Drugs for the enhancement of synaptic plasticity such as the following types:
nicotinic receptor antagonists such as mecamylamine; and
mixed 5-HT, dopamine and norepinephrine receptor agonists such as lurasidone.

(55) Drugs used for the treatment of ADHD such as amphetamine; 5-HT receptor modulators such as vortioxetine and alpha-2 adrenoceptor agonists such as clonidine.

(56) Neutral endopeptidase (NEP) inhibitors such as sacubitril, omapatrilat; and

(57) Methylene blue (MB).

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g., preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g., Janet S. Dodd, ed., The ACS Style Guide: A Manual for Authors and Editors, 2$^{nd}$ Ed., Washington, D.C.: American Chemical Society, 1997, herein incorporated in its entirety by reference. The compounds described herein were prepared according to: Roberts et al. (*Bioorg. Med. Chem. Lett.*, 21, 6515-6518 (2011)).

Example 1: Compounds Syntheses

Intermediate 1 (1-((2-Methylpyrimidin-5-yl) methyl)-1H-pyrazolo[3,4-b]pyridine-3-carbonitrile)

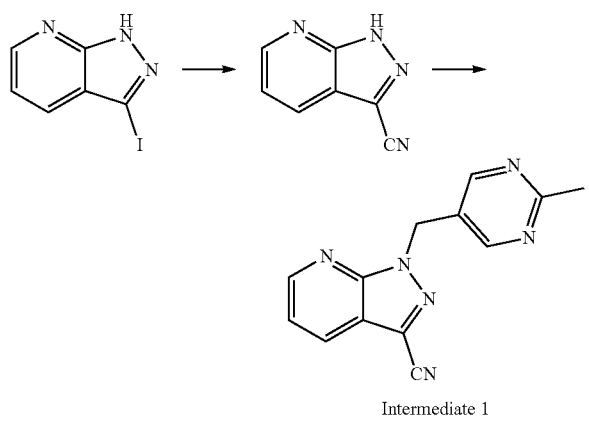

Intermediate 1

The title compound was synthesized in 2 steps.

Step 1: Synthesis of 1H-pyrazolo[3,4-b]pyridine-3-carbonitrile

Zinc(II) cyanide (1.0 g, 8.6 mmol) and 2-iodo-1H-pyrazolo [3,4-b]pyridine (1.4 g, 5.7 mmol) were mixed in DMF (40 mL) at ambient temperature and a stream of nitrogen was bubbled through the solution for 5 minutes. [1,1'-Bis(diphenylphosphino)ferrocene]dichloro-palladium(II) dichloromethane complex (Pd(dppf)Cl$_2$·CH$_2$Cl$_2$) (0.33 g, 0.40 mmol) was added and the solution was degassed for another 10 minutes. The reaction was maintained under a positive nitrogen atmosphere and heated at 130° C. for 48 hours. The mixture was cooled to ambient temperature, filtered and the residue was washed with ethyl acetate. The combined filtrates were concentrated in vacuo onto Celite® and purified by column chromatography (20 to 70% EtOAc/hexanes gradient) to afford the title compound as a light yellow solid (0.51 g, 62% yield).

$^1$H NMR (500 MHz, methanol-d$_4$) δ (ppm) 8.67 (dd, 1H), 8.34 (dd, 1H), 7.44 (dd, 1H).

Step 2: Synthesis of 1-((2-methylpyrimidin-5-yl) methyl)-1H-pyrazolo[3,4-b]pyridine-3-carbonitrile A solution of triphenylphosphine (0.19 g, 0.72 mmol) in DCM/THF (1:1, 4.0 mL) was cooled to 0° C. and diisopropylazodicarboxylate (DIAD) (0.14 mL, 0.72 mmol) was added dropwise over 2 minutes. After 30 minutes, the reaction mixture was added to a solution of (2-methylpyrimidin-5-yl)methanol (0.09 g, 0.72 mmol) and 1H-pyrazolo [3,4-b]pyridine-3-carbonitrile (0.08 g, 0.56 mmol) in THF (4.0 mL) at 0° C. The resultant mixture was allowed to warm to ambient temperature over 3 hours. The reaction was diluted with ethyl acetate (100 mL) and washed with water (3×10 mL) and brine. The organic phase was dried over Na$_2$SO$_4$, filtered and concentrated in vacuo. Purification by column chromatography (25 to 100% EtOAc/hexanes gradient) afforded the title compound as a white solid (89 mg, 64% yield).

$^1$H NMR (500 MHz, chloroform-d) δ (ppm) 8.81 (s, 2H), 8.72 (dd, 1H), 8.23 (dd, 1H), 7.41 (dd, 1H), 5.77 (s, 2H), 2.74 (s, 3H).

The following related intermediates were either commercially available or synthesized according to literature methods (Roberts, L. R. et al. *Bioorg. Med. Chem. Lett.* 2011, 21, 6515-6518).

1-(2-Fluorobenzyl)-1H-pyrazolo[3,4-b]pyridine-3-carbonitrile;

8-(2-Fluorobenzyl)imidazo[1,5-a]pyrimidine-6-carbonitrile;

7-(2-Fluorobenzyl)imidazo[1,5-b]pyridazine-5-carbonitrile;

1-((2-Methylpyrimidin-5-yl)methyl)imidazo[1,5-a]pyridine-3-carbonitrile;

1-(Pyrimidin-5-ylmethyl)imidazo[1,5-a]pyridine-3-carbonitrile; and 1-(2-Fluorobenzyl)imidazo[1,5-a]pyridine-3-carbonitrile.

Compound I-1

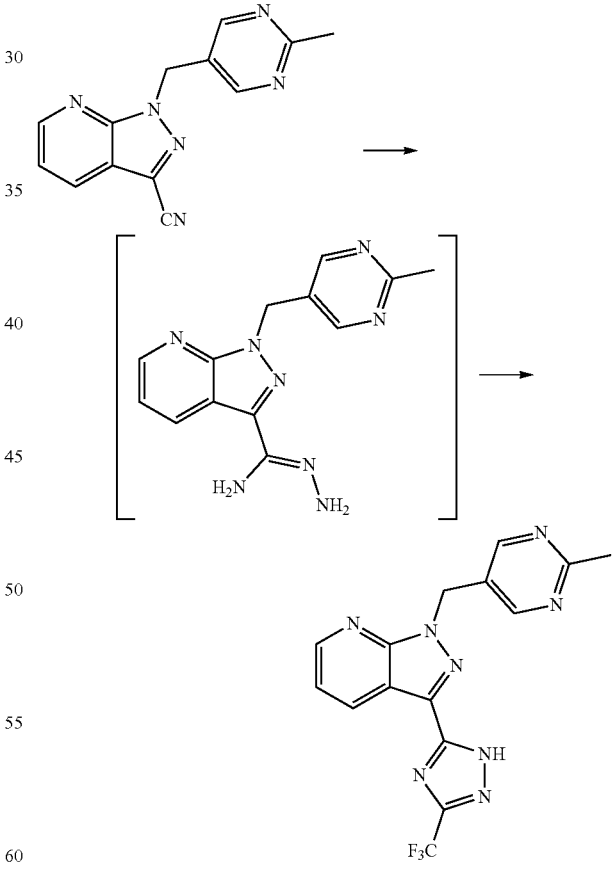

Compound I-1

This compound was synthesized by General Procedure A:

To a solution of 1-((2-methylpyrimidin-5-yl)methyl)-1H-pyrazolo[3,4-b]pyridine-3-carbonitrile (Intermediate 1, 85 mg, 0.34 mmol) in absolute ethanol (3.0 mL) (note: anhydrous methanol could also be used as a solvent) was added anhydrous hydrazine (0.10 g, 3.2 mmol). After stirring at ambient temperature for 3 days and then at 60° C. 1 day, complete disappearance of starting material was observed. The reaction was concentrated in vacuo and the residue was dried in vacuo overnight. The residue was taken up in DCM (5.0 mL) and 2,2,2-trifluoroacetic anhydride (0.05 mL, 0.34 mmol) was added dropwise. The reaction was stirred at ambient temperature until complete consumption of the amidrazone intermediate. Toluene (5.0 mL) was added followed by dropwise addition of phosphoryl trichloride (0.10 mL, 1.0 mmol).

The resultant mixture was heated at 65° C. for 30 min in a sealed vial. The reaction mixture was poured into EtOAc (100 mL) and washed with 10% aqueous NaHCO$_3$ solution (2×10 mL) and brine (10 mL). The organic layer was dried over Na$_2$SO$_4$, filtered and concentrated in vacuo. Purification by column chromatography (30 to 100% EtOAc/hexanes gradient) afforded the title compound as a white solid (74 mg, 60% yield).

$^1$H NMR (500 MHz, chloroform-d) δ (ppm) 14.5 (br s, 1H), 9.03 (s, 2H), 8.83 (dd, 1H), 8.72 (dd, 1H), 7.40 (dd, 1H), 5.84 (s, 2H), 2.87 (s, 3H).

Compound I-2

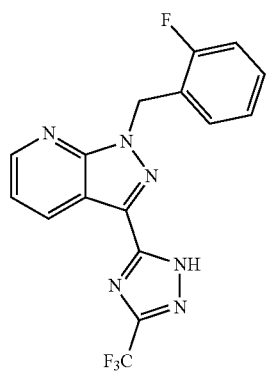

Compound I-2

Synthesized according to General Procedure A as a white solid (54 mg, 40% yield). The reaction conditions (such as reagents ratio, temperature and reaction time) were modified as needed.

$^1$H NMR (500 MHz, DMSO-d$_6$) δ (ppm) 15.7 (br s, 1H), 8.76 (dd, 1H), 8.67 (dd, 1H), 7.50 (dd, 1H), 7.37 (m, 1H), 7.24 (m, 1H), 7.21 (m, 1H), 7.16 (app. t, 1H), 5.90 (s, 2H).

Compound I-3

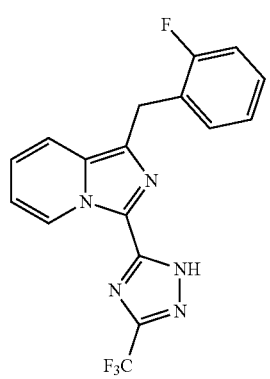

Compound I-3

Synthesized according to General Procedure A as a white solid (85 mg, 58% yield). The reaction conditions (such as reagents ratio, temperature and reaction time) were modified as needed.

$^1$H NMR (500 MHz, methanol-d$_4$) δ (ppm) 9.29-9.35 (m, 1H), 7.63-7.69 (m, 1H), 7.29-7.35 (m, 1H), 7.19-7.26 (m, 1H), 6.92-7.11 (m, 4H), 4.35 (d, 2H).

Compound I-4

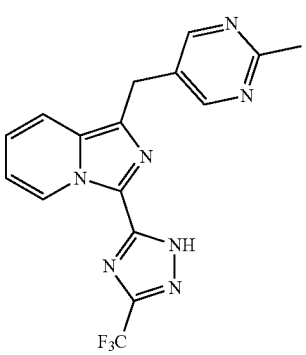

Compound I-4

Synthesized according to General Procedure A as a white solid (34 mg, 58% yield). The reaction conditions (such as reagents ratio, temperature and reaction time) were modified as needed.

$^1$H NMR (500 MHz, DMSO-d$_6$) δ (ppm) 15.6 (br s, 1H), 9.22 (d, 1H), 8.67 (s, 2H), 7.96 (d, 1H), 7.10 (m, 2H), 4.33 (s, 2H), 2.56 (s, 3H).

Compound I-5

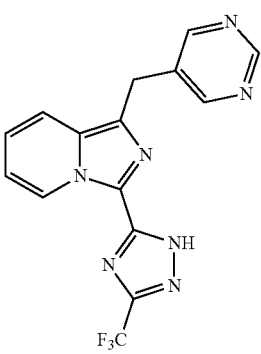

Compound I-5

Synthesized according to literature methods (Roberts, L. R. et al. *Bioorg. Med. Chem. Lett.* 2011, 21, 6515-6518) as a tan solid (800 mg). The reaction conditions (such as reagents ratio, temperature and reaction time) were modified as needed.

$^1$H NMR (500 MHz, DMSO-d$_6$) δ (ppm) 15.60 (s, 1H), 9.22 (d, 1H), 9.05 (s, 1H), 8.80 (s, 2H) 7.99 (d, 1H), 7.08-7.14 (m, 2H), 4.40 (s, 2H).

Compound I-6

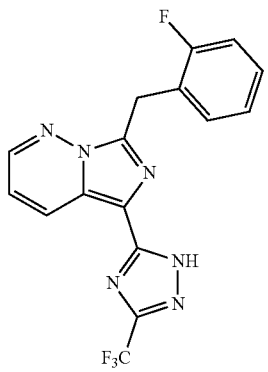

Compound I-6

Synthesized according to General Procedure A as a yellow solid (12 mg, 24% yield). The reaction conditions (such as reagents ratio, temperature and reaction time) were modified as needed.

$^1$H NMR (500 MHz, methanol-$d_4$) δ (ppm) 8.58 (dd, 1H), 8.36 (dd, 1H), 7.25-7.33 (m, 2H), 7.07-7.13 (m, 2H), 6.99 (dd, 1H), 4.58 (s, 2H).

Compound I-7

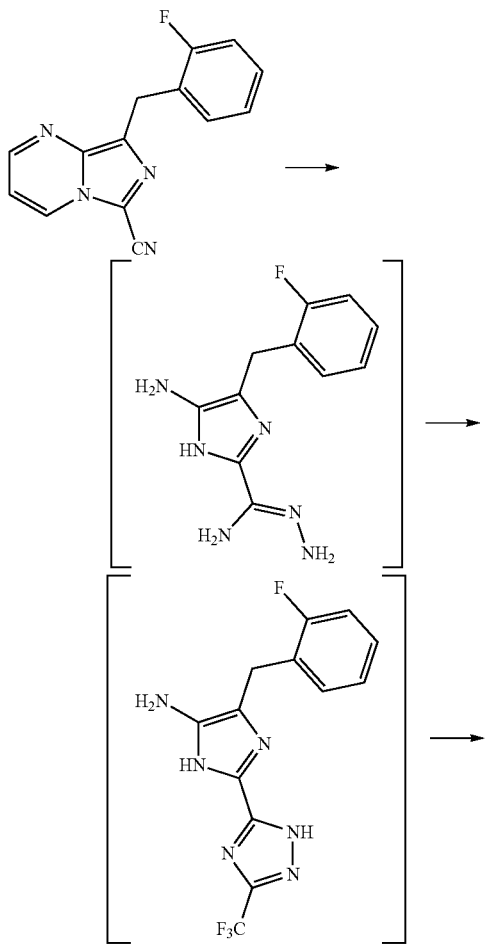

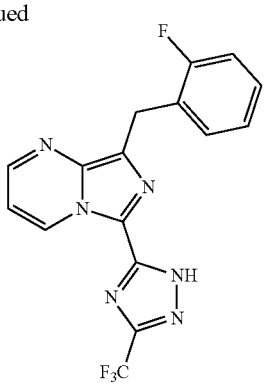

Compound I-7

To a solution of 8-(2-fluorobenzyl)imidazo[1,5-a]pyrimidine-6-carbonitrile (110 mg, 0.44 mmol) in anhydrous methanol (3.0 mL) was added anhydrous hydrazine (0.08 mL, 2.7 mmol). After stirring at ambient temperature for 46 hours, complete disappearance of starting material was observed. The reaction was concentrated in vacuo and the residue was dried in vacuo overnight. The residue (5-amino-4-(2-fluorobenzyl)-1H-imidazole-2-carboximidohydrazide) was taken up in THF (3.0 mL) and 2,2,2-trifluoroacetic anhydride (0.07 mL, 0.54 mmol) was added dropwise. Additional amount of 2,2,2-trifluoroacetic anhydride (0.05 mL, 0.36 mmol) was added to drive to complete consumption of the amidrazone intermediate. The reaction was concentrated in vacuo and the residue was dissolved in DCM/toluene (1:1 ratio, 6.0 mL) followed by dropwise addition of phosphoryl trichloride (0.13 mL, 1.3 mmol). The reaction mixture was heated at 75° C. overnight in a sealed vial. After cooling to ambient temperature, aqueous NaOH solution (1.0 N, 15 mL) and DCM (20 mL) were added. After stirring for 3 days, the resultant mixture was neutralized to pH ~6-7 with 6.0 N HCl solution and extracted with DCM/iso-propanol (5:1 ratio, 4×30 mL). The combined organic layers were dried over $Na_2SO_4$, filtered and concentrated to afford a brown oil. The residue (4-(2-fluorobenzyl)-2-(3-(trifluoromethyl)-1H-1,2,4-triazol-5-yl)-1H-imidazol-5-amine) was taken up in absolute ethanol (4.0 mL) and treated with 1,1,3,3-tetramethoxypropane (0.37 mL, 2.2 mmol). After heating for 5 hours in a microwave, additional amount of 1,1,3,3-tetramethoxypropane (0.18 mL, 1.1 mmol) was added and the mixture was heated in a microwave for an additional 6 hours. The reaction mixture was concentrated in vacuo and the residue was purified using reverse phase preparative HPLC (30-80% acetonitrile/water gradient with 0.1% formic acid as additive) to isolate the title compound (6.4 mg, 4.0% yield) as a tan solid.

$^1$H NMR (500 MHz, DMSO-$d_6$) δ (ppm) 15.8 (br s, 1H), 9.42 (dd, 1H), 8.45 (dd, 1H), 7.31-7.23 (m, 2H), 7.19-7.14 (m, 2H), 7.09 (app. t, 1H), 4.38 (s, 2H).

The syntheses of Compounds I-8 to I-16 are described in Roberts, L. R. et al. *Bioorg. Med. Chem. Lett.* 2011, 21, 6515-6518.

Example 2: Biological Activity Measurement by the cGMP GloSensor Cell-Based Assay, 384-Well Format Human embryonic kidney cells (HEK293) cells expressing GloSensor™ 40F cGMP (Part No: CS182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GloSensor cells were maintained in Dulbecco's Modification of Eagle's Medium (DMEM) supplemented with fetal bovine serum (FBS, 10% final) and hygromycine (200 ug/ml). The day before assay, cells were plated in DMEM with 10% FBS in a 50 μL volume at a density of $1.5 \times 10^4$ cells/well in a poly-D-lysine coated 384-well flat white-bottom plate (Corning Cat No 35661). Cells were incubated overnight at 37° C. in a humidified chamber with 5% $CO_2$. The next day, medium was removed and cells were replaced with 40 ul/well of GboSensor™, 2 mM (Promega Cat No E1291). Cells were treated for 90 minutes at 25° C. to allow the substrate to equilibrate in the cells. Test compounds and Diethylenetriamine NONOate (DETA-NONOate) was diluted to 3 mM (20×) in serum-free $CO_2$ independent medium and serially diluted at 4× dilutions to create 5× dose curve from which 10 ul was added to the wells (x μM concentration for test compound solution and 10 μM concentration for DETA-NONOate solution; wherein x is one of the following final concentrations: 30 μM, 7.5 μM, 1.9 μM, 469 nM, 117 nM, 29.3 nM, 7.3 nM, 1.83 nM, 0.46 nM, 0.11 nM, 0.03 nM)

For the kinetics studies, luminescense was measured right away for 0.2 sec per well with Envision (Perkin Elmer). For endpoint SAR screening, data were collected after 55 min incubation at room temperature.

Data were normalized to a high control using the following equation: 100*(Sample−Low Control)/(High Control−Low Control), where the low control is the average of 16 samples treated with 1% DMSO, and the high control is the average of 16 samples treated with 30 μM of Compound Y depicted below. Data were fit using a 4-parameter fit (log (agonist) vs. response—variable slope) using GraphPad Prism Software v.5. n=2 for all compounds. The Absolute (Abs) $EC_{50}$ was interpolated from the curve fit and is defined as the concentration at which a given compound elicits 50% of the high control response after data normalization as indicated above. Compounds failing to elicit a minimum response of 50% are reported as >30 μM or ND. For compounds run in duplicate or n higher than 2, the result herein given is the geometric mean of the several results obtained. Table 2 summarizes results obtained for selected compounds of the invention in this assay.

Compound Y

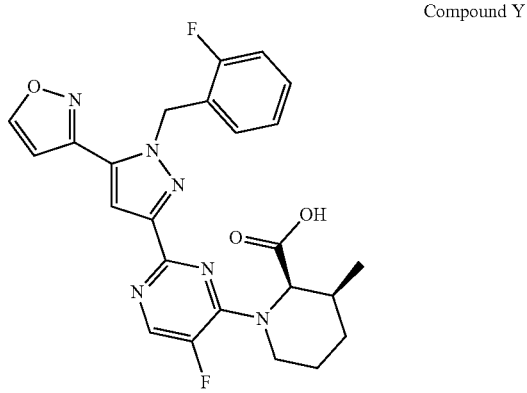 [SMILES: C[C@H]1CCCN(c2nc(-c3cc(-c4ccon4)n(Cc4ccccc4F)n3)ncc2F)[C@H]1C(=O)O]

TABLE 2

Whole cell activity in the GloSensor cell-based assay, 384-well format (Example 2) for compounds in Table I.

| Compound | Glo sensor Abs EC50 (nM) |
|---|---|
| I-5 | B |
| I-2 | A |
| I-6 | B |
| I-4 | B |
| I-3 | B |
| I-7 | B |
| I-1 | B | sGC enzyme activity values in HEK cells, determined by the GloSensor assay.
(~) Code definitions for the sGC enzyme activity values, expressed as Absolute $EC_{50}$ which is defined as the concentration at which a given compound elicits 50% of the high control response (Compound Y) after data normalization: Abs $EC_{50} \leq 10$ nM = A; 10 nM < Abs $EC_{50} \leq 100$ nM = B; 100 nM < Abs $EC_{50}$ = C. Compounds failing to elicit a minimum response of 50% are reported as >30 μM or ND.

Example 3. Biological Activity Measurement by the cGMP Neuronal Cell-Based Assay Rat primary neurons were isolated from fetuses of 18-day pregnant Sprague-Dawley females. The fetuses were collected in Hanks' balanced salt solution (HBSS) and brains were rapidly removed. The cerebral hippocampi were isolated and mechanically fragmented. Further tissue digestion was performed with 0.25% (wt/vol) trypsin solution in HBSS without Ca2+ and Mg2+ for 15 min at 37° C. After trypsination, cells were washed and resuspended in neurobasal medium supplemented with 0.5 mM L-glutamine, 12.5 uM glutamic acid, 2% B-27 and 100 U/mL penicillin, and 100 μg/mL streptomycin. Cells were plated at a density of $4 \times 10^4$ cells/well in a poly-D-lysine coated 384-well flat clear-bottom plate (Corning Cat No 354662). Cells were incubated 6-7 days at 37° C. in a humidified chamber with 5% $CO_2$. Media was removed and cells were washed 1× with HBSS containing Ca2+ and Mg2+, and replaced with 40 uL HBSS containing 0.5 mM IBMX, and incubated for 15 minutes at 37° C. 10 uL of a 5× stock of test compounds with diethylenetriamine NONOate (DETA-NO) was added. Final concentration of DETA-NO was 30 μM. Cells were incubated for 20 min at 37° C. Medium was removed, 50 uL of ice-cold 10% acetic acid was added, and incubated for 60 minutes at 4° C. Following centrifugation at 4° C. for 5 minutes at 1000×g to pellet cell debris, the supernatant was aspirated to a clean plate and the samples were analyzed for cGMP content. cGMP concentrations were determined from each sample using LC-MS/MS.

Data were normalized to a high control using the following equation: 100*(Sample−Low Control)/(High Control−Low Control), where the low control is the average of 15 samples treated with 1% DMSO, and the high control is the average of 15 samples treated with 10 μM of the known sGC stimulator Compound Y (depicted in Example 2). Data were fit using a 4-parameter fit (log(agonist) vs. response—variable slope) using GraphPad Prism Software v.5. n=2 for all compounds. The Absolute $EC_{50}$ was interpolated from the curve fit and is defined as the concentration at which a given compound elicits 50% of the high control response after data normalization. Compounds failing to elicit a minimum response of 50% are reported as >30 μM. For compounds run in duplicate or n higher than 2, the result herein given is the geometric mean of the several results obtained. Table 3 summarizes results obtained for selected compounds of the invention in this assay.

TABLE 3

Biological activity in the cGMP neuronal cell-based assay (Example 3) for compounds in Table I.

| Compound | sGC-neuron Abs EC50 (nM) |
|---|---|
| I-5 | A |
| I-2 | A |
| I-3 | A |

Neuronal-based cell assay. AbsEC$_{50}$ ≤ 100 nM = A; 100 nM < AbsEC$_{50}$ ≤ 1000 nM = B; 1000 nM < AbsEC$_{50}$ = C. Compounds failing to elicit a minimum response of 50% are reported as >30 μM or ND.

Example 4: Rat Cerebrospinal Fluid (CSF) Pharmacokinetic Properties Protocol PK in rats was determined following oral dosing. For the oral (PO) experiments, a group of 6 male Sprague-Dawley rats with an indwelling catheter placed in the cisterna magna were used. The PO group was dosed with 3 or 10 mg/kg of a compound formulated as a solution in PEG400. PO doses were administered by oral gavage and delivered to the stomach using a syringe and gavage tube. Following oral dosage administration, the gavage tube was flushed with approximately 0.5 mL of water to ensure complete delivery of the full dose.

Plasma and CSF samples were collected as follows: samples of CSF and blood were collected at 1 hour and 2 hours post-dosing. CSF samples (0.05 mL) were collected through the intracisternal catheter. Blood samples (0.25 mL) were collected through retro-orbital sampling. These samples were kept on ice until processed for plasma. Blood samples were centrifuged at 3200 rpm for 5 minutes at approximately 5° C. within 1 hour of collection. Plasma was directly transferred to a 96-well plate tube (0.125 mL). Plug caps were placed on the tubes and the tubes frozen at approximately −70° C. and stored until analysis.

Plasma was collected and analyzed for the presence of compound.

Quantitation of Compounds

The compound in question and the internal standard were extracted from plasma and CSF by precipitation. Samples were analyzed using liquid chromatography (LC) with tandem mass spectrometric detection (MS/MS) using electrospray ionization. The standard curve range was from 1 to 1000 ng/mL. Results of the compounds described herein in this assay are illustrated in Table 4 below.

Kp,uu is defined as the concentration ratio of unbound drug in CSF to unbound drug in plasma. Unbound drug in plasma (or free plasma concentration) is calculated by multiplying the total plasma concentration by the unbound fraction as determined by plasma protein binding. The CSF concentration is then divided by the free plasma concentration to determine the Kp,uu. (See e.g., Di et al., *J. Med. Chem.*, 56, 2-12 (2013)).

TABLE 4

CSF PK properties of select compounds described herein (Example 4) for compounds in Table I (at a 10 mg/kg dose)

| Compound | CSF Conc (nM @ 1 h) | Kp, uu (@ 1 h) |
|---|---|---|
| I-5 | 446 | 3.26 |
| I-2 | 62.9 | 3.16 |
| I-6 | 0.78 | <0.01 |
| I-4 | 180 | 0.96 |

Example 5: Evaluation of Compounds of the Invention on Synaptic Transmission and Plasticity Impairments in R6/2 Mice Hippocampal Slices Improvements in synaptic transmission and plasticity, as measured by long term potentiation (LTP), is believed to indicate the potential of a compound to enhance memory. LTP is an electrophysiological phenomena that is commonly referred to as the a cellular phenomenon driving learning and memory.

Protocol.

Preparation of acute mice hippocampal slices. Experiments were carried out with 11 to 12 week-old R6/2 and WT mice provided by the Jackson Laboratory (USA). Hippocampal slices (350 μm thickness) were cut with a MacIlwain tissue chopper in an ice-cold oxygenated sucrose solution (Saccharose 250, Glucose 11, NaHCO$_3$ 26, KCl 2, NaH$_2$PO$_4$ 1.2, MgCl$_2$ 7, and CaCl$_2$ 0.5 in mM). The slices were incubated 1 hour at room temperature in ACSF of the following composition: Glucose 11, NaHCO$_3$ 25, NaCl 126, KCl 3.5, NaH$_2$PO$_4$ 1.2, MgCl$_2$ 1.3, and CaCl$_2$ 2 in mM. Then, the slices were let to recover for at least 1 h.

Slice perfusion and temperature control. During the experiments, the slices were continuously perfused with the ACSF (bubbled with 95% O$_2$-5% CO$_2$) at the rate of 3 mL/min with a peristaltic pump (MEA chamber volume: ~1 mL). Complete solution exchange in the MEA chamber was achieved 20 s after the switch of solutions. The perfusion liquid was continuously pre-heated at 37° C. just before reaching the MEA chamber with a heated-perfusion cannula (PH01, MultiChannel Systems, Reutlingen, Germany). The temperature of the MEA chamber was maintained at 37±0.1° C. with a heating element located in the MEA amplifier headstage.

Stimulation Protocols/Compound Application.

Input/Output (I/O) curve: from 100 to 800 μA, by 100 μA steps. The stimulus intensity was then set to a fixed value of 250 μA for the short- and long-term synaptic plasticity measurements.

Short-term plasticity properties: two pulses with a decreasing inter-stimuli interval (e.g. 300 ms, 200 ms, 100 ms, 50 ms, 25 ms) were applied. Compound application: fEPSP were recorded for 10 minutes in control conditions (to verify the baseline steadiness) followed by a 15-minute exposure to the compound (or 25 minutes in the presence of vehicle only for control slices). A second I/O protocol and paired-pulse protocol were applied, as described previously, in the continuous presence of the compound.

Long-Term Potentiation (LTP): Following a 10-minute control period (in the presence of the compound or vehicle for control slices), LTP was induced by a 10×TBS. Potentiation of synaptic transmission was then monitored for an additional 60-minute period (in the continuous presence of the compound or vehicle for control slices).

Results

I/O Characteristics were significantly higher (p-value=0.0146, two-way ANOVA) after exposure to 855 nM Compound I-5 in R6/2 hippocampal slices. Paired-pulse properties were significantly increased (p-value<0.001, two-way ANOVA) after exposure to 855 nM Compound I-5 in R6/2 hippocampal slices. Exposure to 855 nM of Compound I-5 for 15 minutes did not modify fEPSP amplitude.

In WT mice hippocampal slices (control conditions), HFS triggered a potentiation of the evoked-response amplitudes that stabilized around 35% (fEPSP were increased by 36±3%, at endpoint). In R6/2 mice hippocampal slices (control conditions), HFS triggered a potentiation of the evoked-response amplitudes that stabilized around 15% (fEPSP were increased by 15±2%, at endpoint). After exposure to 855 nM Compound I-5, HFS triggered a potentiation of the evoked response amplitude around 40% (fEPSP were increased by 40±6%, at endpoint). (FIG. 1) Thus, the potentiation in R6/2 slices was significantly increased (p-value=0.0002, two-way ANOVA) compared to R6/2 control slices.

Conclusions.

I/O characteristics and paired-pulse properties were increased after exposure to 855 nM Compound I-5 in R6/2 mice hippocampal slices. 855 nM of Compound I-5 was devoid of effect on basal synaptic transmission on R6/2 mice hippocampal slices, for a 15-minute exposure period. The LTP deficit of hippocampal R6/2 slices was restored to the amplitude level of LTP of WT hippocampal slices after exposure to 855 nM Compound I-5.

Example 6: Compound-Induced cGMP in Mouse Brain

Objective. To determine the effect of a compound of the invention in cGMP response in different areas of the mouse brain (cortex, hippocampus, cerebellum and striatum).

Protocol. Mice (n=9-10 per experimental condition) were dosed P.O. with vehicle (1% hydroxypropyl methyl cellulose, 0.2% Tween80, 0.5% methyl cellulose), P.O. with 10 mg/Kg of Compound I-2. Thirty minutes after dosing, under isoflurane anesthesia, each mouse was decapitated and its brain was removed and was placed into an ice-cold petri dish containing slushy dissection solution (saturated with 95% $O_2 \cdot 5\%$ $CO_2$). Using an ice-cold spatula, the brain was transferred to mouse brain matrix with coronal spacing for slicing at 1 mm intervals, as schematized in the FIGURE below (not to scale, just a scheme).

The sliced brain was transferred back into petri dish containing slushy dissection solution with IBMX 0.5 mM (saturated with 95% $O_2 \cdot 5\%$ $CO_2$). The dorsal striatum is dissected first, followed by the hippocampus second, followed by the medial prefrontal cortex third, and lastly, the cerebellum fourth. After each region was dissected the "chunk" of tissue was immediately placed into an eppendorf which had been placed on dry ice for the previous 30 minutes. Small pieces of tissue froze very fast, within 10 seconds approximately. After all regions were placed in an eppendorf, eppendorfs were snap frozen by immersion into liquid nitrogen. The tissue samples were stored at −80 C. cGMP levels in brain were determined by LC/MS. Brain samples were homogenized in an aqueous buffer consisting of 80:20 (V/V %) water:acetic acid using an ultrasonicator probe. Brain homogenates containing sGC compounds and or cGMP were extracted from brain tissue by protein precipitation with an organic solvent containing internal standards (IS) followed by filtration and phospholipid removal using a Phenomenex® Phree™ phospholipid removal plate. Samples were analyzed using liquid chromatography (LC) with tandem mass spectrometric detection (MS/MS) using electrospray ionization. The standard curve concentrations used for quantitation of cGMP and or sGC compound(s) ranged from 0.2 to 400 ng/mL. Protein quantification of brain samples was determined using BCA protein assay kit.

Conclusion. Acute dosing of 10 mg/Kg Compound I-2 P.O. in mice induced a significant increase of cGMP in the hippocampus (ANOVA p=0.0022; Vehicle versus Compound I-2 p=0.0035), cerebellum (ANOVA p<0.0001; Vehicle versus Compound I-2 p=0.0001) and cortex (ANOVA p=0.012; Vehicle versus Compound I-2 p=0.017).

TABLE 6a

The concentration of cGMP in the mouse hippocampus normalized to protein concentration in the samples.
Hippocampus: nM cGMP/μg protein

| Vehicle P.O. | Compound I-2 P.O. (10 mg/Kg) |
|---|---|
| 0.033 | 0.072 |

TABLE 6b

The concentration of cGMP in the mouse striatum normalized to protein concentration in the samples.
Striatum: nM cGMP/μg protein

| Vehicle P.O. | Compound I-2 P.O. (10 mg/Kg) |
|---|---|
| 0.062 | 0.104 |

TABLE 6c

The concentration of cGMP in the mouse cerebellum normalized to protein concentration in the samples.
Cerebellum: nM cGMP/μg protein

| Vehicle P.O. | Compound I-2 P.O. (10 mg/Kg) |
|---|---|
| 0.364 | 0.681 |

TABLE 6d

The concentration of cGMP in the mouse cortex normalized to protein concentration in the samples.
mPFC: nM cGMP/μg protein

| Vehicle P.O. | Compound I-2 P.O. (10 mg/Kg) |
|---|---|
| 0.075 | 0.124 |

Example 7. Novel Object Recognition (NOR) Test

Objective. To assess the efficacy of compounds of the invention in reversing memory disruption induced by MK-801 using the Novel Object Recognition (NOR) test in male Long Evans rats. The NOR is a test of recognition learning and memory retrieval, which takes advantage of the spontaneous preference of rodents to investigate a novel object compared with a familiar one (Ennaceur and Delacour, 1988). Studies indicated that the NOR procedure involves several brain regions, including perirhinal cortex (Ennaceur et al. 1996, 1997 and Aggleton et al. 1997) and the hippocampus (Wood et al. 1993 and Clark et al. 2000). The NOR test has been employed extensively to assess the potential cognitive-enhancing properties of novel test compounds. Because the NOR paradigm does not involve reward or noxious stimuli, it provides less confounding variables when being translated into analogous tests conducted in human clinical trials. In the present study, a memory saving model was used to test the novel compound—MK-801 (Dizocilpine), an uncompetitive antagonist of the NMDA receptor was used to cause deficit of recognition memory. Compounds of the invention were evaluated through its efficacy in reversing memory impairment.

Material and Methods.

Animals. Adult male Long-Evans rats (275-299 gram at arrival from Envigo, Indianapolis, Ind.) were used in this study. Rats were placed in the experimental rooms and assigned unique identification numbers (tail marks). Rats were housed 2 per cage in polycarbonate cages with filter tops and acclimated for at least 7 days prior to testing. Animal room was maintained in a 12/12 h light/dark cycle (lights on at 07.00 EST), 22±1° C. and relative humidity at approximately 50%. Food and water were provided ad libitum. All animals were examined, handled and weighed prior to the study to assure adequate health and to minimize the non-specific stress associated with testing. Each animal was randomly assigned across the treatment groups. The experiments were conducted during the animal's light cycle phase.

Test compounds. The following compounds were used in this study:

MK-801 (0.1 mg/kg; Sigma-Aldrich) was dissolved in saline and injected IP 15 min prior to NOR training.

Galantamine (1 mg/kg; Tocris) was dissolved in saline and injected IP 15 minutes prior to training.

Compound I-2 (0.1, 1, and 10 mg/kg) was oral administrated 60 minutes prior to training. Vehicle was 0.5% Methylcellulose, 0.2% Tween and 1% HPMC in filtered water. The dose volume was 4 ml/kg Experimental procedures. NOR test was conducted in an open-field arena (40×40 cm) placed in a sound-attenuated room under dimmed lighting. Each rat was tested separately and care was taken to remove olfactory/taste cues by cleaning the arena and test objects with 70% alcohol between trials and rats. All training and testing trials were videotaped and scored by an observer blind to treatments.

On Days 1 and 2, rats were allowed to freely explore the arena (no objects inside) for a 5-minute habituation period. On Day 3 (training and testing day), rats were administered vehicle (saline), galantamine or compound solutions followed by MK-801 or vehicle (saline). After the pretreatment time, each animal was placed into the test arena in the presence of two identical objects. Each rat was placed in the arena facing the same direction at the same position, and the time spent actively exploring the objects during a 3-minute training period (T1) was recorded. The rat was returned to its home cage following training. NOR test (T2) was conducted 1 hours after T1. Each rat was placed back into the test arena in the presence of one familiar object and one novel object for 5 minutes, and the time spent exploring both objects was recorded during 0-1, 0-3 and 0-5 min time ranges. The presentation order and position of the objects (left/right) in T2 was randomized between rats to prevent bias from order or place preference.

Statistical Analysis. Data of NOR test (T2) were expressed as Recognition Index, which is defined as the ratio of the time spent exploring the novel object over the total time spent exploring both objects (Novel/(Familiar+Novel)× 100%) during the test session. Data were analyzed by using one-way ANOVA followed by Fisher's LSD post hoc test on 0-1, 0-3 and 0-5 minute time range separately, with significance set at $P<0.05$. Animals with overall object exploration time less than 10 seconds in the 5 min test session were eliminated; rats with recognition index above 90% or below 30% were also eliminated because they suggest strong (non-memory) bias between two objects. And then statistical outliers that fell above or below two standard deviations from the mean were removed from the final analysis.

Results. None of the rats in this study showed obvious side effects at any dose. Rats maintained normal vigilance, activity and exploration level to objects. ANOVA showed insignificant main treatment effects on Recognition Index during 0-1 min time range [$F(5.79)=1.305$, $P>0.05$], mainly because the MK-801-treated rats maintained relatively good recognition memory at this time range. This result at 0-1 min is not rare in this version of NOR because at the beginning of the test as "novelty" and "familiarity" of the objects are relative clear. Usually the rats perform progressive worse in MK-801 group unless a memory enhancer is applied. During the 0-3 minute time range, ANOVA found a significant main treatment effect [$F(5.79)=4.237$, $P<0.01$]. Post hoc test showed that MK-801 0.1 mg/kg caused a strong memory deficit, with a Recognition Index approaching chance level (50%). Galantamine (1 mg/kg) and Compound I-2 at 0.1 mg/kg significantly reversed MK-801-induced memory deficits ($P<0.001$ and $P<0.05$, respectively, compared to Vehicle/MK-801 group). Similarly, ANOVA showed a significant main treatment effect during the 0-5 minute time range [$F(5.79)=3.851$, $P<0.01$]. Post hoc test showed that MK-801 at 0.1 mg/kg caused a strong memory deficit, with a Recognition Index approaching chance level (50%). Galantamine (1 mg/kg) and Compound I-2 at 0.1 mg/kg significantly reversed MK-801-induced memory deficits ($P<0.001$ and $P<0.05$, respectively, compared to Vehicle/MK-801 group).

TABLE 10

Summary of Recognition Index Measurements (0 to 3 minute time bin)

| Treatment | n-number | Mean | Standard Deviation | Standard Error of the Mean | Statistical Analysis (p-value) |
|---|---|---|---|---|---|
| Vehicle + Saline Control | 13 | 73.78 | 9.95 | 2.761 | <0.001 |
| Vehicle + MK-801 | 13 | 56.92 | 13.93 | 3.86 | N/A |
| Galantamine + MK-801 | 14 | 73.33 | 9.34 | 2.50 | <0.001 |
| I-2 (0.1 mg/kg) + MK-801 | 13 | 68.21 | 11.99 | 3.33 | 0.017 |
| I-2 (1 mg/kg) + MK-801 | 14 | 63.98 | 10.41 | 2.78 | 0.125 |
| I-2 (10 mg/kg) + MK-801 | 13 | 61.76 | 14.54 | 4.03 | 0.299 |

Statistical comparisons are made to the "Vehicle+MK-801" treatment group. Statistical significance is deemed when p value is less than 0.05.

Summary. The reference compound galantamine (1 mg/kg) significantly reversed the cognitive deficit induced by MK-801 0.1 mg/kg, suggesting the validity of the test. Test compound I-2 at 0.1 mg/kg also showed efficacy in saving the NOR memory after treatment of MK-801, suggesting this compound possess properties of memory enhancement.

Example 8: pCREB Phosphorylation in Rat Primary Neurons

Objective. To assess the ability of Compound I-5 to activate cAMP response element-binding protein (CREB) in rat primary neurons. CREB is a cellular transcription factor. It binds to DNA sequences called cAMP response elements (CRE), and regulates transcription of the downstream genes (See Bourtchuladze R, et al., Cell 1994; 79 (1): 59-68).

CREB has a well-documented role in neuronal plasticity and long-term memory formation in the brain and has been shown to be integral in the formation of spatial memory (See Silva A J, et al., Annual Review of Neuroscience 1998; 21: 127-148). CREB proteins are activated by phosphorylation of Serine 133 by various kinases, including cAMP-dependent protein kinase or Protein Kinase A (PKA), cGMP-dependent protein kinase or Protein Kinase G (PKG), and Ca2+/calmodulin-dependent protein kinases. (See Shaywitz A J and Greenberg M E, Annual Review of Biochemistry 1999; 68 (1): 821-861 and Wong J C, et al., J Cell Biochem 2012: 113(11):3587-98). Stimulation of CREB could have therapeutic benefits for diseases in which cognition, neuronal plasticity, and or neuronal function is impaired.

Materials and Methods.

Compounds. Compound I-5 was dissolved in DMSO as a 10 mM solution and stored at −20° C. To achieve desired test concentrations, stock concentrations were serially diluted into DMSO and then diluted to the appropriate concentration in assay buffer.

Rat primary neurons culture. Neurons were isolated from Sprague Dawley rat embryos on embryonic day 18 (E18). Approximately 10 embryos were obtained from each rat, and whole brains were isolated from the embryos. Hippocampus and cortex were dissected from the brains under a stereoscopic microscope using two pairs of fine tweezers. The meninges were carefully removed. After dissection, the tissues were chopped and washed gently once with 10 mL of $Ca^{2+}$ and $Mg^{2+}$ free Hank's solution (HBSS, Corning cat #21-022-CM) in a 15-mL conical tube. After washing, 5 mL of a solution of 0.25% trypsin (Invitrogen cat #15090-046) and 0.1% deoxyribonuclease I (DNase I, Sigma cat #DN-25) were added to the tissues in the tube, which were then incubated at 37° C. for 15 min. After incubation and digestion with the enzymes, tissues were washed three times with ice-cold HBSS. After washing, 3 mL of a solution of 0.1% of DNase I was added to the tube and the tissues were slowly pipetted using a glass Pasteur pipette 12 times, and then centrifuged at 500×g for 10 min. The cell pellet was resuspended in the culture medium (Neurobasal medium, Gibco cat #21103-049), 2% of B27 supplement (Gibco Cat #17504-044), 0.5 mM L-glutamine (Corning cat #25-005-C1), 25 μM L-glutamic acid (Sigma cat #G1251) and 1% penicillin/streptomycin (Gibco cat #15070-063)). Subsequently, the cell suspension was plated into poly-L-lysine coated 96-well plates at 100,000 cells/well. Twenty-four h after plating, half of the culture medium was removed and replaced with culture medium as described above but without glutamic acid. Cells were maintained in a 37° C. humidified incubator with 5% $CO_2$ and used between days 6-10.

Assay Conditions. For each test concentration, Compound I-5 was diluted in 100% DMSO to 100-fold of its final assay concentration. Immediately prior to the assay, Compound I-5 was diluted 10-fold into HBSS (containing calcium and magnesium) (10× the final assay concentration) containing 100 μM DETA-NONOate (10× the final assay concentration). Medium was removed and cells were washed once with 90 μL HBSS (Corning cat #21-023-CV). Cells were then incubated with 90 μL HBSS for 30 min at 37° C. 10 μL from the test article/HBSS/DETA-NONOate plate was added to the cells, which were incubated for additional 30 min at 37° C. Final DMSO concentrations were 1%, final DETA-NONOate concentration was 30 μM; and final Compound I-5 concentrations were 10,000 nM, 1000 nM, 100 nM, 10 nM, 1 nM, 0.1 nM, 0.01 nM, and 0.0 nM. Medium was removed and cell were lysed and assay was performed according to Cisbio protocol (phospho-CREB (Ser133) catalog #64CREPEG) and the plate was read using Envision instrument (PerkinElmer).

Data Analysis. Data were analyzed with a 4-parameter fit (log(agonist) vs. response—variable slope) using GraphPad Prism Software v.7. The $EC_{50}$ was interpolated from the curve fit and is defined as the concentration at which Compound I-5 elicits 50% of its maximal response.

Results. Phosphorylation of CREB at Ser133 stimulated by Compound I-5 was concentration-dependent, with an $EC_{50}$ of 0.55 nM. The 95% confidence interval ranged from 0.07 nM to 4.44 nM.

Example 9. Evaluation of Compounds of the Invention in Pain Models and Tests

Objective. To evaluate the efficacy of compounds of the invention in acute and tonic pain, neuropathic pain, inflammatory pain, post-operative pain, and visceral pain.

Materials and Methods:

Paw Pressure Test. Static mechanical hyperalgesia is measured. This test requires the application of an increasing pressure on the hind paws between a flat surface and a blunt pointer. To evaluate the analgesic action of a compound, one hind paw of the animal was inflamed by an injection or injured by ligation, while the other hind paw was not injured or inflamed. The apparatus exerted a steadily increasing force on the hind paws. The reaction threshold was determined as the pressure (g) required to elicit paw withdrawal and/or vocalization. The animals were gently handled by the experimenter and static mechanical hyperalgesia were assessed two times for both hind paws.

Tail Flick Test. A radiant heat was applied on the tail. When the rat felt discomfort, it reacted by a sudden tail movement (tail flick) which automatically stopped the stimulation and the timer for the measurement by the animal reaction time or nociceptive reaction latency (period from the beginning of the stimulation until detection of the response of the animal). A cut-off was previously fixed at 10 sec in order to prevent tissue damage.

Acetic Acid Test. Abdominal contraction was induced by intraperitoneal injection of 0.6% acetic acid solution in rats (10 mL/kg). The number of writhing (a twisting or contorting of the body due to pain) was recorded from the $5^{th}$ to the $15^{th}$ minute after injection.

Formalin Test. 2.5% formalin solution was injected by subplantar route into the right hind paw. Scoring of pain behavior was performed in rats for 36 minutes every 3 minutes according to the following scores:

0=normal behavior of the injected hind limb to support the body
1=slight touching of the injected paw on the floor to lightly support or not support the body
2=total withdrawal of the injected paw
3=licking, biting or shaking of the injected paw.

Bennett Model. Peripheral mononeuropathy was induced by loose ligation of the sciatic nerve in anesthetized rats (Xylazine 10 mg/kg i.p., ketamine 60 mg/kg i.p.) on $D_{-14}$. Briefly, the common sciatic nerve was exposed at the level of the middle of the thigh by blunt dissection through the biceps femoris. Proximal to the sciatic trifurcation, four ligatures were loosely tied around it with about 1-mm spacing. Great care was taken to tie the ligatures, such that the diameter of the nerve was seen to be just barely constricted. After surgery, the animals recovered for 4 days, testing occurred 10 days after recovery period (i.e., 14 days after surgery).

Oxaliplatin. Induction: Acute peripheral neuropathy was induced by a single intraperitoneal injection of oxaliplatin (6 mg/kg, i.p) 30 hours before testing. Acetone test: Cold allodynia was measured using the acetone test. In this test, the latency of hind paw withdrawal was measured after application of a drop of acetone (50 µL) to the plantar surface of both hind paws three times for both hind paws alternatively with intervals of approximately 2-3 min.

Carrageenan. Induction: Three hours before assessment of the nociceptive threshold using the paw pressure test 100 µL of a 2% carrageenan suspension was injected into the plantar aspect of the right hind paw. The Paw Pressure test was then conducted as described above.

Kaolin. Induction: In rats, unilateral arthritis was induced by an intra-articular injection of a 10% kaolin suspension into the knee joint of the right hind paw under gas anesthesia (3.5% isoflurane/3 L/min). Gait score: The gait score will be evaluated 3 h 30 min after kaolin administration by:
0: normal gait
1: mid disability
2: intermittent raising of the paw
3: elevated paw.

Brennan Model. Surgery: Surgery was done under gas anesthesia (2.5% isoflurane/3 L/min). For all rats, the plantar aspect of the left hind paw was exposed and a 1 cm longitudinal incision was made using a surgical blade, through the skin and fascia of the plantar aspect of the foot, starting 0.5 cm from the proximal edge of the heel and extending toward the toes. The plantaris muscle was elevated and incised longitudinally whereas the insertions remained intact. After hemostasis with gentle pressure, the skin was stitched up with two sutures. After surgery, animals recovered in their cages.

Electronic Von Frey Test. Tactile allodynia was assessed using the electronic Von Frey test 24 h after surgery. The test requires the application of an increasing pressure onto the plantar aspect of the hind paws. The apparatus exerted a steady force on the hind paws. Reaction thresholds were determined as the pressure (g) required to elicit paw withdrawal. Each reaction threshold measurement was repeated three times for both hind paws with intervals of approximately 2 to 3 mins.

TNBS. Surgery: Colonic sensitivity was induced by surgical administration of TNBS seven days before behavioral testing ($D_{-7}$). Fasted (overnight) animals underwent surgery. Briefly, under anesthesia (Xylazine 10 mg/kg i.p., ketamine 60 mg/kg i.p.), injection of TNBS (50 mg/kg, 1 mL/kg) was performed into the proximal part of the colon (1 cm from the caecum). After surgery, animals returned in their home cages in a regulated environment, and were fed ad libitum until $D_{-1}$ (animals were fasted 24 hours before distention). Colorectal distension: Seven days ($D_0$) after TNBS injection, colonic sensitivity was assessed on fasted (overnight) animals by measuring the intra-colonic pressure required to induce a behavioral response during colonic distension. To perform distension, a 5-cm balloon was gently inserted into the colon of vigil animals at 10 cm from the anus and the catheter was taped to the base of the tail. After a 30 min acclimation period with the inserted balloon, colonic pressure was gradually increased by 5 mm Hg steps every 30 sec from 5 to 75 mm Hg (cut off) until pain behavior is evidenced. Pain behavior was characterized by an elevation of the hind part of the animals body and a clearly visible abdominal contraction corresponding to a severe cramp. Two determinations were performed.

The results for acute and tonic pain, neuropathic pain, inflammatory pain, post-operative pain, and visceral pain models and test for animals treated with 10 mg/kg of Compound I-2 PO were significant and are presented below.

Results.

| Pain Model | Model-test | Compound I-2, p.o., 10 mg/kg % of activity vs. vehicle | Reference ID | Internal Reference % of activity vs. vehicle |
|---|---|---|---|---|
| Acute and Tonic Pain | Healthy rats-paw pressure test | −10% | Morphine 4 mg/kg s.c. | 69% |
| | Healthy rats-tail flick test | 15% | Morphine 4 mg/kg s.c. | 66% |
| | Acetic acid test-Abdominal cramps | 59% | (−) U50, 488 H 3 mg/kg s.c. | 100% |
| | Formalin test-Score (early phase) | 61% | Morphine 4 mg/kg s.c. | 57% |
| | Formalin test-Score (late phase) | 11% | Morphine 4 mg/kg s.c. | 38% |
| Neuropathic Pain | Bennett model-Paw pressure test | 65% | Morphine 3 mg/kg s.c. | 191% |
| | Oxaliplatin-Acetone test (reaction time) | 127% | Gabapentin 100 mg/kg, po | 82% |
| Inflammatory Pain | Carrageenan-paw pressure test | 75% | Indomethacin 30 mg/kg p.o. | 100% |
| | Kaolin-gait score | 88% | Indomethacin 10 mg/kg p.o. | 58% |
| Post-operative Pain | Brennan model-Electronic Von Frey test | 16% | Morphine 4 mg/kg s.c. | 88% |
| Visceral Pain | TNBS-Colorectal distension | 43% | (−) U50, 488 H 3 mg/kg s.c. | 103% |

Testing: 120 minutes after treatment. N=4/model/test. Results are expressed for each group as a percentage of activity calculated from the mean value of the vehicle-treated animals and compared to naïve animals, control paw, or cut-off value, depending on the test.

Conclusions. Compound I-2 demonstrated effects in the acetic acid and formalin tests for acute pain. Compound I-2 demonstrated effects in the Bennett model/Paw pressure test and Oxaliplatin-Acetone test models of neuropathic pain. Compound I-2 demonstrated effects in the carrageenan-paw pressure test and the kaolin-gait score models of inflammatory pain. Compound I-2 demonstrated effects in the Brennan model—Electronic Von Frey test model for post-operative pain. Compound I-2 demonstrated effects in the TNBS-Colorectal distension test model for visceral pain.

Example 10. Dose-Response Compound-Induced cGMP in Mouse Brain

Objective. To determine the effect of different doses of a compound of the invention in cGMP response in the mouse brain (cerebrum)

Protocol. Experimental Day 1: Fast mice overnight with ad libitum access to water. Experimental Day 2: Mice (n=10 per experimental condition) were dosed P.O. with vehicle (1% hydroxypropyl methyl cellulose, 0.2% Tween80, 0.5% methyl cellulose), 3 or 10 mg/Kg of Compound I-2 prepared in vehicle. Thirty minutes after dosing, under isoflurane anesthesia, each mouse was decapitated and its brain was removed. The cerebrum was separated from each brain and placed in separate 15 ml falcon tubes and flash froze by immersion into liquid nitrogen. The tissue samples were stored at −80 C. cGMP levels in brain were determined by LC/MS. Brain samples were homogenized in an aqueous buffer consisting of 80:20 (V/V %) water:acetic acid using an ultrasonicator probe. Brain homogenates containing sGC compounds and or cGMP were extracted from brain tissue by protein precipitation with an organic solvent containing internal standards (IS) followed by filtration and phospholipid removal using a Phenomenex® Phree™ phospholipid removal plate. Samples were analyzed using liquid chromatography (LC) with tandem mass spectrometric detection (MS/MS) using electrospray ionization. The standard curve concentrations used for quantitation of cGMP and or sGC compound(s) ranged from 0.2 to 400 ng/mL. Protein quantification of brain samples was determined using BCA protein assay kit Conclusion. Acute dosing of Compound I-2 at 10 and 3 mg/Kg P.O. increases cGMP in mouse brain as compared to vehicle dosed animals ($p<0.0001$ and $p<00.31$, ANOVA followed by planned comparisons).

Example 11: Effect on BDNF Protein in the Rat Dorsal Striatum

Objective. To determine the effect of Compound I-2 treatment in the expression of BDNF in the rat striatum, in a model of quinolinic acid induced brain lesion Protocol. Experimental day 1: Rats were deeply anesthetized with isoflurane and each rat received a unilateral infusion of 0.25 µl of 50 mM quinolinic acid (QA) in the dorsal striatum (12.5 nmoles of QA on the left or right hemisphere). The dorsal striatum contralateral to the QA infusion on each rat received a control infusion of 0.25 µl PBS (control side). Some animals were dosed S.C. with vehicle (n=5) or 10 mg/Kg Compound I-2 (n=6) about 30 minutes after QA infusion. Experimental days 2-8: Rats were dosed every 24 h P.O. with Vehicle or 10 mg/Kg Compound I-2. About 24 h after the last dosing of vehicle or Compound I-2, rats were anesthetized, perfused with PBS followed by perfusion with 4% Paraformaldehyde in PBS; brain tissue was collected and placed in a falcon tube covered with 4% Paraformaldehyde (PAF) in PBS for about 14 h at 4° C. and then replaced by PBS with 30% sucrose solution for about 48 h. Brain tissue was cut in 40 µm coronal slices and stored in PBS at 4° C. Slices containing dorsal striatum were stained by incubation with mouse anti-NeuN and rabbit anti-BDNF primary antibodies, followed by incubation with anti-rabbit conjugated to Alexa Fluor 594 and anti-mouse conjugated to Alexa Fluor 488 secondary antibodies. Images from the dorsomedial area around the QA lesion or equivalent area on the control hemisphere were taken using confocal fluorescence microscopy. Images were analyzed using imageJ software to determine the average BDNF intensity in NeuN positive cells.

Conclusion. Average intensity of BDNF staining in NeuN positive cells around the QA lesion (QA side) is significantly decreased as compare to NeuN positive cells in the control hemisphere (control side); $p<0.0001$, ANOVA followed by multiple comparisons. Treatment with Compound I-2 at 10 mg/kg once a day for 7 days results in the increase of BDNF averaged intensity in NeuN positive cells around the QA lesion, as compared to vehicle treatment; $p<0.01$, ANOVA followed by multiple comparisons. Treatment with Compound I-2 at 10 mg/kg once a day for 7 days results in the increase of BDNF averaged intensity in NeuN positive cells in the dorsomedial striatum without a lesion (control side), as compared to vehicle treatment; $p<0.0001$, ANOVA followed by multiple comparisons.

Various embodiments of the invention can be described in the text below:

[1]. A compound depicted in Table I, or a pharmaceutically acceptable salt thereof.

[2]. A pharmaceutical composition comprising at least one pharmaceutically acceptable excipient or carrier and a compound or pharmaceutically acceptable salt of [1] above, or according to other embodiments of the invention.

[3]. A dosage form comprising the pharmaceutical composition of [2] above, or according to other embodiments of the invention.

[4]. A method of treating a CNS disease, health condition or disorder in a subject in need thereof, comprising administering, alone or in combination therapy, a therapeutically effective amount of [1], [2], or [3] above, or according to other embodiments of the invention.

[5]. The method of [4] above, or according to other embodiments of the invention, wherein the CNS disease is selected from Alzheimer's disease (AD), amyotrophic lateral sclerosis (ALS or Lou Gehrig's disease), Down's syndrome, dementia, vascular dementia (VD), vascular cognitive impairment, mixed dementia, Binswanger's dementia (subcortical arteriosclerotic encephalopathy), cerebral autosomal-dominant arteriopathy with subcortical infarcts and leukoencephalopathy (CADASIL or CADASIL syndrome), frontotemporal lobar degeneration or dementia, HIV-associated dementia (including asymptomatic neurocognitive impairment (ANI), minor neurocognitive disorder (MND), and HIV-associated dementia (HAD) (also called AIDS dementia complex [ADC] or HIV encephalopathy), Lewy body dementia, pre-senile dementia (mild cognitive impairment or MCI), glaucoma, Huntington's disease (or Huntington's chorea, HD), multiple sclerosis (MS), multiple system atrophy (MSA), Parkinson's disease (PD), Parkinsonism Plus, spinocerebellar ataxias, Steel-Richardson-Olszewski disease (progressive supranuclear palsy), attention deficit disorder (ADD) or attention deficit hyperactivity disorder (ADHD).

[6]. The method of [5] above, or according to other embodiments of the invention, wherein the CNS disease is Alzheimer's disease.

[7]. The method of [6] above, or according to other embodiments of the invention, wherein the mild to moderate Alzheimer's disease or moderate to severe Alzheimer's disease.

[8.] The method of [5] above, or according to other embodiments of the invention, wherein the CNS disease is vascular dementia. The method of [5] above, or according to other embodiments of the invention, wherein the CNS disease is mixed dementia.

[9]. The method of [5] above, or according to other embodiments of the invention, wherein the CNS disease is Huntington's disease.

[10]. The method of [5] above, or according to other embodiments of the invention, wherein the CNS disease is Parkinson's.

[11]. The method of [5] above, or according to other embodiments of the invention, wherein the CNS disease is CADASIL.

[12]. The method of [5] above, or according to other embodiments of the invention, wherein the CNS disease is mild cognitive impairment.

[13]. The method of [4] above, or according to other embodiments of the invention, wherein the CNS disease is selected from either traumatic (closed or open) penetrating head injuries, traumatic brain injury (TBI), non-traumatic injury to the brain, stroke, (in particular, ischemic stroke), aneurism, hypoxia, cognitive impairment or dysfunction resulting from brain injuries or neurodegenerative disorders.

[14]. The method of [4] above, or according to other embodiments of the invention, wherein the CNS disease is selected from a dystonia, including generalized, focal, segmental, sexual, intermediate, genetic/primary dystonia or acute dystonic reaction; or a dyskinesia, including acute, chronic/tardive, or non-motor and levo-dopa induced dyskinesia (LID).

[15]. The method of [4] above, or according to other embodiments of the invention, wherein the CNS disease is a psychiatric, mental, mood or affective disorder selected from a bipolar disorder, schizophrenia, general psychosis, drug-induced psychosis, a delusional disorder, a schizoaffective disorder, obsessive compulsive disorder (OCD), a depressive disorder, an anxiety disorder, a panic disorder or post-traumatic stress disorder (PTSD).

[16]. The method of [4] above, or according to other embodiments of the invention, wherein the CNS disease is selected from disorders characterized by a relative reduction in synaptic plasticity and synaptic processes including Fragile X, Rhett's disorder, Williams syndrome, Renpenning's syndrome, autism spectrum disorders (ASD), autism, Asperger's syndrome, pervasive development disorder or childhood disintegrative disorder.

[17]. The method of [4] above, or according to other embodiments of the invention, wherein the CNS disorder is selected from chemo brain, levo-dopa induced addictive behavior, alcoholism, narcotic dependence, including to amphetamine, opiates or other substances or substance abuse.

[18]. [1], [2], or [3] above, or according to other embodiments of the invention, for use in treating a CNS disease.

[19]. Use of [1], [2], or [3] above, or according to other embodiments of the invention, for the treatment of a CNS disease.

While typical embodiments have been set forth for the purpose of illustration, the foregoing descriptions and examples should not be deemed to be a limitation on the scope of the invention. Accordingly, various modifications, adaptations, and alternatives may occur to one skilled in the art without departing from the spirit and scope of the present invention.

The invention claimed is:

1. A method of enhancing memory or reversing memory disruption or impairment in a subject in need thereof, comprising administering, alone or in combination therapy, a therapeutically effective amount of a compound or a pharmaceutically acceptable salt thereof to the subject in need thereof, wherein the compound is selected from those depicted in Table I, or a pharmaceutically acceptable salt thereof, or a pharmaceutical composition or a dosage form comprising said compound or pharmaceutically acceptable salt thereof:

TABLE I

| Structure | Compound Number |
|---|---|
| 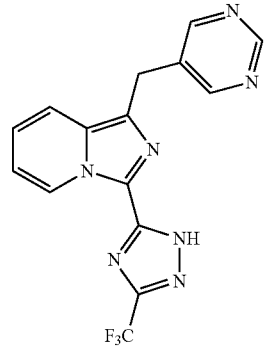 [SMILES: FC(F)(F)c1n[nH]c(-c2nc(Cc3cncnc3)c3ccccn23)n1] | I-5 |
| 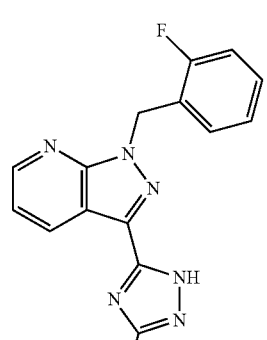 | I-2. |

2. A method of improving or restoring synaptic transmission and neuronal plasticity, or improving long term potentiation in a subject in need thereof, comprising administering, alone or in combination therapy, a therapeutically effective amount of a compound or a pharmaceutically acceptable salt thereof to the subject in need thereof, wherein the compound is selected from those depicted in Table I, or a pharmaceutically acceptable salt thereof, or a pharmaceutical composition or a dosage form comprising said compound or pharmaceutically acceptable salt thereof:

TABLE I

| Structure | Compound Number |
|---|---|
| 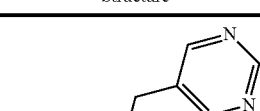 | I-5 |

TABLE I-continued

| Structure | Compound Number |
|---|---|
| [chemical structure: 1-(2-fluorobenzyl)-3-(3-(trifluoromethyl)-1H-1,2,4-triazol-5-yl)-1H-pyrazolo[3,4-b]pyridine] | I-2. |

* * * * *